US011045516B2

(12) United States Patent
Park

(10) Patent No.: US 11,045,516 B2
(45) Date of Patent: Jun. 29, 2021

(54) COMPOSITIONS FOR PREVENTING OR TREATING DISEASES OR DISORDERS ASSOCIATED WITH NEURO-INFLAMMATION, NEURO-APOPTOSIS, OR NEURO-OXIDATIVE DAMAGE AND USES THEREOF

(71) Applicant: Byung-Jun Park, Suncheon-si (KR)

(72) Inventor: Byung-Jun Park, Suncheon-si (KR)

( * ) Notice: Subject to any disclaimer, the term of this patent is extended or adjusted under 35 U.S.C. 154(b) by 0 days.

(21) Appl. No.: 16/653,596

(22) Filed: Oct. 15, 2019

(65) Prior Publication Data
US 2020/0113960 A1   Apr. 16, 2020

Related U.S. Application Data

(60) Provisional application No. 62/745,906, filed on Oct. 15, 2018.

(51) Int. Cl.
| *A61K 36/65* | (2006.01) |
| *A61K 36/74* | (2006.01) |
| *A61K 36/284* | (2006.01) |
| *A61K 36/076* | (2006.01) |
| *A61K 36/234* | (2006.01) |
| *A61P 25/16* | (2006.01) |
| *A61K 36/54* | (2006.01) |
| *A61K 36/258* | (2006.01) |
| *A61K 36/484* | (2006.01) |
| *A61K 36/67* | (2006.01) |
| *A61K 36/48* | (2006.01) |
| *A61K 36/725* | (2006.01) |

(52) U.S. Cl.
CPC .......... *A61K 36/65* (2013.01); *A61K 36/076* (2013.01); *A61K 36/234* (2013.01); *A61K 36/258* (2013.01); *A61K 36/284* (2013.01); *A61K 36/48* (2013.01); *A61K 36/484* (2013.01); *A61K 36/54* (2013.01); *A61K 36/67* (2013.01); *A61K 36/725* (2013.01); *A61K 36/74* (2013.01); *A61P 25/16* (2018.01)

(58) Field of Classification Search
None
See application file for complete search history.

(56) References Cited

PUBLICATIONS

An, Hua et al. "Protective effects of Gastrodia elata Blume on MPP+-induced cytotoxicity in human dopaminergic SH-SY5Y cells." J. Ethnopharmacol. 2010, 130, 290-298.
Baek, Seung Yeop et al. "Protective effect of a novel herbmedicine, Hepad, on apoptosis of SH-SY5Y cells and a rat model of Parkinson's disease." Mol. Cell. Toxicol. 2015, 11, 223-230.
Blum, David et al. "Molecular pathways involved in the neurotoxicity of 6-OHDA, dopamine and MPTP: Contribution to the apoptotic theory in Parkinson's disease." Prog. Neurobiol. 2001, 65, 135-172.
Cao, Qin et al. "Amentoflavone protects dopaminergic neurons in MPTP-induced Parkinson's disease model mice through PI3K/Akt and ERK signaling pathways." Toxicol. Appl. Pharmacol. 2017, 319, 80-90.
Davis, Roger J. "Signal transduction by the JNK group of MAP kinases." Cell 2000, 103, 239-252.
Dehmer, Thomas et al. "Protection by pioglitazone in the MPTP model of Parkinson's disease correlates with I kappa B alpha induction and block of NF kappa B and iNOS activation." J. Neurochem. 2004, 88, 494-501.
Dickens, Martin et al. "A cytoplasmic inhibitor of the JNK signal transduction pathway." Science 1997, 277, 693-696.
Ding, Hongqun et al. "Asiatic acid prevents oxidative stress and apoptosis by inhibiting the translocation of -Synuclein into mitochondria." Front. Neurosci. 2018, 12, 431.
Doo, Ah-Reum et al. "Bee venom protects SH-SY5Y human neuroblastoma cells from 1-methyl-4-phenylpyridinium-induced apoptotic cell death." Brain Res. 2012, 1429, 106-115.
Eberhardt, Olaf et al. "Apoptotic mechanisms and antiapoptotic therapy in the MPTP model of Parkinson's disease." Toxicol. Lett. 2003, 139, 135-151.
Elmore, Susan. "Apoptosis: A review of programmed cell death." Toxicol. Pathol. 2007, 35, 495-516.
Feng, Guoshuai et al. "Protective effect of chinonin in MPTP-induced C57BL/6 mouse model of Parkinson's disease." Biol. Pharm. Bull. 2014, 37, 1301-1307.
Fiskum, Gary et al. "Mitochondrial mechanisms of neural cell death and neuroprotective interventions in Parkinson's disease." Ann. N. Y. Acad. Sci 2003, 991, 111-119.
Gan, Ping et al. "Anti-inflammatory effects of glaucocalyxin B in microglia cells. J. Pharmacol. Sci. 2015, 128, 35-46.".
González-Scarano, Francisco et al. "Microglia as mediators of inflammatory and degenerative diseases." Annu. Rev. Neurosci 1999, 22, 219-240.
Grimmig, Beth et al. "Astaxanthin is neuroprotective in an aged mouse model of Parkinson's disease." Oncotarget. 2018, 9, 10388-10401.
Shim, Jin Sup et al. "Effects of the hook of Uncaria rhynchophylla on neurotoxicity in the 6-hydroxydopamine model of Parkinson's disease." J. Ethnopharmacol. 2009, 126, 361-365.

(Continued)

Primary Examiner — Susan Hoffman
(74) Attorney, Agent, or Firm — Wilson Sonsini Goodrich & Rosati

(57) ABSTRACT

Provided herein are compositions for treating a disorder or a disease associated with or characterized by neuro-inflammation, neuro-apoptosis, or neuro-oxidative damage in a subject, pharmaceutical compositions comprising the compositions and pharmaceutically acceptable excipients, and pharmaceutical formulations comprising the compositions. Provided also herein are methods of treating a disorder or a disease associated with or characterized by neuro-inflammation, neuro-apoptosis, or neuro-oxidative damage in a subject, and methods of regulating inflammation, antioxidant enzymes, and apoptosis in a subject having a disorder or a disease associated with or characterized by neuro-inflammation, neuro-apoptosis, or neuro-oxidative damage.

7 Claims, 21 Drawing Sheets

(56) References Cited

PUBLICATIONS

Janhom, Prachya et al. "Neuroprotective Effects of Alpha-Mangostin on MPP+-Induced Apoptotic Cell Death in Neuroblastoma SH-SY5Y Cells." J. Toxicol. 2015.

Jeohn, Gwang-Ho et al. "p38 MAP kinase is involved in lipopolysaccharide-induced dopaminergic neuronal cell death in rat mesencephalic neuron-glia cultures." Ann. N. Y. Acad. Sci. 2002, 962, 332-346.

Jeong, Jin-Woo et al. "Ethanol extract of Poria cocos reduces the production of inflammatory mediators by suppressing the NF-kappaB signaling pathway in lipopolysaccharide-stimulated RAW 264.7 macrophages." BMC Complement. Altern. Med. 2014, 14, 101.

Kim, Byung-Wook et al. "alpha-Asarone attenuates microglia-mediated neuroinflammation by inhibiting NF kappa B activation and mitigates MPTP-induced behavioral deficits in a mouse model of Parkinson's disease." Neuropharmacology 2015, 97, 46-57.

Kim, In-Su et al. "Protective effect of Chrysanthemum indicum Linne against 1-methyl-4-phenylpridinium ion and lipopolysaccharide-induced cytotoxicity in cellular model of Parkinson's disease." Food Chem. Toxicol. 2011, 49, 963-973.

Kim, Ji Hyun et al. "Effects of methanol extract of Uncariae Ramulus et Uncus on ibotenic acid-induced amnesia in the rat." J. Pharmacol. Sci. 2004, 96, 314-323.

Kim, Jin et al. "Paeonia japonica, Houttuynia cordata, and Aster scaber water extracts induce nitric oxide and cytokine production by lipopolysaccharide-activated macrophages." J. Med. Food 2009, 12, 365-373.

Kim, Myeong II et al. "Application of centrifugal partition chromatography for bioactivity-guided purification of antioxidant-response-element-inducing constituents from Atractylodis Rhizoma Alba." Molecules 2018, 23, 2274.

Kitamura, Yoshihisa et al. "Protective effects of the antiparkinsonian drugs talipexole and pramipexole against 1-methyl-4-phenylpyridinium-induced apoptotic death in human neuroblastoma SH-SY5Y cells." Mol. Pharmacol. 1998, 54, 1046-1054.

Knaryan, Varduhi H. et al. "SNJ-1945, a calpain inhibitor, protects SH-SY5Y cells against MPP(+) and rotenone." J. Neurochem. 2014, 130, 280-290.

Lev, Nirit et al. "Apoptosis and Parkinson's disease." Prog. Neuropsychopharmacol. Biol. Psychiatry 2003, 27, 245-250.

Li, Like et al. "Changes in blood anti-oxidation enzyme levels in MPTP-treated monkeys." Neurosci. Lett. 2017, 649, 93-99.

Li, Tie-Jun et al. "Protective effects of Guizhi-Fuling-Capsules on rat brain ischemia/reperfusion injury." J. Pharmacol. Sci. 2007, 105, 34-40.

Lim, Hye-Sun et al. "The Anti-neuroinflammatory Activity of Tectorigenin Pretreatment via Downregulated NF-kB and ERK/JNK Pathways in BV-2 Microglial and Microglia Inactivation in Mice with Lipopolysaccharide." Front. Pharmacol. 2018, 9, 462.

Liu, Bin et al. "Role of microglia in inflammation-mediated neurodegenerative diseases: Mechanisms and strategies for therapeutic intervention." J. Pharmacol. Exp. Ther. 2003, 304, 1-7.

Liu, Yigang et al. "MANF improves the MPP+/MPTP-induced Parkinson's disease via improvement of mitochondrial function and inhibition of oxidative stress." Am. J. Transl Res. 2018, 10, 1284-1294.

McGeer, Edith G. et al. "The role of anti-inflammatory agents in Parkinson's disease." CNS Drugs 2007, 21, 789-797.

Nam, Kyung-Soo et al. "Effect of Cnidii Rhizoma on nitric oxide production and invasion of human colorectal adenocarcinoma HT-29 cells." Oncol. Lett. 2015, 9, 483-487.

Niranjan, Rituraj et al. "The mechanism of action of MPTP-induced neuroinflammation and its modulation by melatonin in rat astrocytoma cells, C6." Free Radic. Res. 2010, 44, 1304-1316.

Nishioku, Tsuyoshi et al. "Tumor necrosis factor-alpha mediates the blood-brain barrier dysfunction induced by activated microglia in mouse brain microvascular endothelial cells." J. Pharmacol. Sci. 2010, 112, 251-254.

Offen, Daniel et al. "Apoptosis as a general cell death pathway in neurodegenerative diseases." J. Neural. Transm. Suppl. 2000, 58, 153-166.

Patil, Sachin P. et al. "Neuroprotective effect of metformin in MPTP-induced Parkinson's disease in mice." Neuroscience 2014, 277, 747-754.

Perier, Celine et al. "Mitochondria and programmed cell death in Parkinson's disease: Apoptosis and beyond." Antioxid. Redox Signal. 2017, 16, 883-895.

Takata, Kazuyuki et al. "Molecular approaches to the treatment, prophylaxis, and diagnosis of Alzheimer's disease: Tangle formation, amyloid-beta, and microglia in Alzheimer's disease." J. Pharmacol. Sci. 2012, 118, 331-337.

Tansey, Malú G. et al. "Neuroinflammatory mechanisms in Parkinson's disease: Potential environmental triggers, pathways, and targets for early therapeutic intervention." Exp. Neurol. 2007, 208, 1-25.

Tseng, Yu-Ting et al. "The Chinese herbal formula Liuwei dihuang protects dopaminergic neurons against Parkinson's toxin through enhancing antioxidative defense and preventing apoptotic death." Phytomedicine 2014, 21, 724-733.

Turmel, Hélène et al. "Caspase-3 activation in 1-methyl-4-phenyl-1,2,3,6-tetrahydropyridine (MPTP)-treated mice." Mov. Disord. 2001, 16, 185-189.

Xia, Lei et al. "Neuroprotective effects of astragaloside IV on Parkinson disease models of mice and primary astrocytes." Exp. Ther. Med. 2017, 14, 5569-5575.

Xu, Ming Lu et al. "Antioxidant and Anti-diabetes Activity of Extracts from *Machilus thunbergii* S. et Z." Korean J. Med. Crop Sci. 2010, 18, 34-39. (Abstract in English).

Xu, Qi et al. "Neuroprotective effect of the natural iron chelator, phytic acid in a cell culture model of Parkinson's disease." Toxicology 2008, 245, 101-108.

Yan, Aijuan et al. "Partial Depletion of Peripheral M1 Macrophages Reverses Motor Deficits in MPTP-Treated Mouse by Suppressing Neuroinflammation and Dopaminergic Neurodegeneration." Front. Aging Neurosci. 2018, 10, 160.

Yan, Junqiang et al. "Simvastatin prevents dopaminergic neurodegeneration in experimental parkinsonian models: The association with anti-inflammatory responses." PLoS ONE 2011, 6, e20945.

Yang, Jie et al. "Prevention of apoptosis by Bcl-2: Release of cytochrome c from mitochondria blocked." Science 1997, 275, 1129-1132.

Yu, Song et al. "Curcumin prevents dopaminergic neuronal death through inhibition of the c-Jun N-terminal kinase pathway." Rejuv. Res. 2010, 13, 55-64.

Yue, Peijian et al. "Pretreatment of glial cell-derived neurotrophic factor and geranylgeranylacetone ameliorates brain injury in Parkinson's disease by its anti-apoptotic and anti-oxidative property." J. Cell. Biochem. 2018, 119, 5491-5502.

Zeng, Guang et al. "Salvianolic acid B protects SH-SY5Y neuroblastoma cells from 1-methyl-4-phenylpyridinium-induced apoptosis." Biol. Pharm. Bull. 2010, 33, 1337-1342.

Zhong, Jiahong et al. "Inhibition of phosphodiesterase 4 by FCPR16 protects SH-SY5Y cells against MPP+-induced decline of mitochondrial membrane potential and oxidative stress." Redox Biol. 2018, 16, 47-58.

COMPOSITIONS FOR PREVENTING OR TREATING DISEASES OR DISORDERS ASSOCIATED WITH NEURO-INFLAMMATION, NEURO-APOPTOSIS, OR NEURO-OXIDATIVE DAMAGE AND USES THEREOF

CROSS-REFERENCE TO RELATED APPLICATION

The present application claims the benefit of U.S. Provisional Patent Application No. 62/745,906 filed Oct. 15, 2018, which is hereby incorporated by reference in its entirety.

TECHNICAL FIELD

The present invention related to compositions for and methods of treating diseases or disorders associated with or characterized by neuro-inflammation, neuro-apoptosis or neuro-oxidative damage, neurological diseases, or neurodegenerative diseases.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein are compositions, pharmaceutical compositions, pharmaceutical formulations, nutraceutical compositions, and nutraceutical formulations for treating a disorder or a disease associated with or characterized by neuro-inflammation, neuro-apoptosis, or neuro-oxidative damage in a subject. Also provided herein are methods of treating a disorder or a disease associated with or characterized by neuro-inflammation, neuro-apoptosis, or neuro-oxidative damage in a subject, methods of reducing, alleviating, ameliorating, attenuating or delaying a sign or a symptom of a disorder or a disease associated with or characterized by neuro-inflammation, neuro-apoptosis, or neuro-oxidative damage in a subject, and methods of regulating inflammation, antioxidant enzymes, and apoptosis in a subject having a disorder or a disease associated with or characterized by neuro-inflammation, neuro-apoptosis, or neuro-oxidative damage. Also provided herein are methods of preparing compositions, pharmaceutical compositions, pharmaceutical formulations, nutraceutical compositions, and nutraceutical formulations for treating a disorder or a disease associated with or characterized by neuro-inflammation, neuro-apoptosis, or neuro-oxidative damage in a subject.

In embodiments, provided herein are compositions for treating a disorder or a disease associated with or characterized by neuro-inflammation, neuro-apoptosis, or neuro-oxidative damage in a subject. In embodiments, the composition comprises an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the composition comprises an effective amount of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject. In embodiments, the composition comprises an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the composition comprises an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the disorder or the disease associated with or characterized by neuro-inflammation, neuro-apoptosis, or neuro-oxidative damage to be treated by the composition is a neurological disease. In embodiments, the disorder or the disease associated with or characterized by neuro-inflammation, neuro-apoptosis, or neuro-oxidative damage to be treated by the composition is a neurodegenerative disease. In embodiments, the disorder or the disease associated with or characterized by neuro-inflammation, neuro-apoptosis, or neuro-oxidative damage to be treated by the composition is an aging-associated neurodegenerative disease. In embodiments, the disorder or the disease associated with or characterized by neuro-inflammation, neuro-apoptosis, or neuro-oxidative damage to be treated by the composition is Parkinson's disease (PD). In embodiments, the sign or the symptom to be reduced, alleviated, ameliorated, attenuated or delayed by the composition is a neuronal cell death, an inflammation, an oxidative stress, a motor deficit, or a combination thereof.

In embodiments, the composition for treating a disorder or a disease associated with or characterized by neuro-inflammation, neuro-apoptosis, or neuro-oxidative damage in a subject comprises the herbal extract mixture prepared by extracting the herbal combination of *Paeonia japonica* and *Uncariae Ramulus* using a solvent. In embodiments, the solvent is an inorganic solvent or an organic solvent. In preferred embodiments, the solvent is water.

In embodiments, the composition for treating a disorder or a disease associated with or characterized by neuro-inflammation, neuro-apoptosis, or neuro-oxidative damage in a subject comprises the herbal extract mixture prepared by extracting the herbal combination of *Atractylodis Rhizoma, Cnidii Rhizoma, Paeonia japonica, Poria cocos* Wolf, *Uncariae Ramulus* Et Uncus, and *Zizyphi Semen* using a solvent. In embodiments, the solvent is an inorganic solvent or an organic solvent. In preferred embodiments, the solvent is water.

In embodiments, the composition for treating a disorder or a disease associated with or characterized by neuro-inflammation, neuro-apoptosis, or neuro-oxidative damage in a subject comprises the herbal extract mixture prepared by extracting the herbal combination of *Paeonia japonica, Uncariae Ramulus* Et Uncus, and *Machilus thunbergii* using a solvent. In embodiments, the solvent is an inorganic solvent or an organic solvent. In preferred embodiments, the solvent is water.

In embodiments, the composition for treating a disorder or a disease associated with or characterized by neuro-inflammation, neuro-apoptosis, or neuro-oxidative damage in a subject comprises the herbal extract mixture prepared by extracting the herbal combination of *Uncariae Ramulus, Paeonia japonica, Machilus thunbergii, Panax ginseng* C. A Meyer, *Glycyrrhiza uralensis, Mucunae caulis* and black pepper using a solvent. In embodiments, the solvent is an inorganic solvent or an organic solvent. In embodiments, the solvent is water.

In embodiments, the composition for treating a disorder or a disease associated with or characterized by neuro-inflammation, neuro-apoptosis, or neuro-oxidative damage in a subject comprises the herbal extract mixture prepared by mixing a combination of an herbal extract of *Paeonia japonica* and an herbal extract of *Uncariae Ramulus* Et Uncus. In embodiments, the composition for treating a disorder or a disease associated with or characterized by neuro-inflammation, neuro-apoptosis, or neuro-oxidative damage in a subject comprises the herbal extract mixture prepared by mixing a combination of an herbal extract of *Atractylodis Rhizoma*, an herbal extract of *Cnidii Rhizoma*, an herbal extract of *Paeonia japonica*, an herbal extract of *Poria cocos* Wolf, an herbal extract of *Uncariae Ramulus* Et Uncus, and an herbal extract of *Zizyphi Semen*. In embodiments, the composition for treating a disorder or a disease associated with or characterized by neuro-inflammation, neuro-apoptosis, or neuro-oxidative damage in a subject comprises the herbal extract mixture prepared by mixing a combination of an herbal extract of *Paeonia japonica*, an herbal extract of *Uncariae Ramulus* Et Uncus, and an herbal extract of *Machilus thunbergii*. In embodiments, the composition for treating a disorder or a disease associated with or characterized by neuro-inflammation, neuro-apoptosis, or neuro-oxidative damage in a subject comprises the herbal extract mixture prepared by mixing a combination of an herbal extract of *Uncariae Ramulus*, an herbal extract of *Paeonia japonica*, an herbal extract of *Machilus thunbergii*, an herbal extract of *Panax ginseng* C. A Meyer, an herbal extract of *Glycyrrhiza uralensis*, an herbal extract of *Mucunae caulis*, and an herbal extract of black pepper. In embodiments, the herbal extract from each herb is prepared by extracting the herb using a solvent. In embodiments, the solvent is an inorganic solvent or an organic solvent. In embodiments, the solvent is water.

In embodiments, the composition for treating a disorder or a disease associated with or characterized by neuro-inflammation, neuro-apoptosis, or neuro-oxidative damage in a subject comprises the herbal extract of *Atractylodis Rhizoma*, the herbal extract of *Cnidii Rhizoma*, the herbal extract of *Paeonia japonica*, the herbal extract of *Poria cocos* Wolf, the herbal extract of *Uncariae Ramulus* Et Uncus, and the herbal extract of *Zizyphi Semen*, wherein each herbal extract is further processed by filtration, concentration, or a combination thereof. In embodiments, the composition for treating a disorder or a disease associated with or characterized by neuro-inflammation, neuro-apoptosis, or neuro-oxidative damage in a subject comprises the herbal extract of *Paeonia japonica*, the herbal extract of *Uncariae Ramulus* Et Uncus, and the herbal extract of *Machilus thunbergii*, wherein each herbal extract is further processed by filtration, concentration, or a combination thereof. In embodiments, the composition for treating a disorder or a disease associated with or characterized by neuro-inflammation, neuro-apoptosis, or neuro-oxidative damage in a subject comprises the herbal extract of *Uncariae Ramulus*, the herbal extract of *Paeonia japonica*, the herbal extract of *Machilus thunbergii*, the herbal extract of *Panax ginseng* C. A Meyer, the herbal extract of *Glycyrrhiza uralensis*, the herbal extract of *Mucunae caulis*, and the herbal extract of black pepper, wherein each herbal extract is further processed by filtration, concentration, or a combination thereof. In embodiments, the composition for treating a disorder or a disease associated with or characterized by neuro-inflammation, neuro-apoptosis, or neuro-oxidative damage in a subject comprises the herbal extract mixture further processed by filtration, concentration, or a combination thereof.

Also provided herein are pharmaceutical compositions comprising the composition comprising an effective amount of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient.

Also provided herein are pharmaceutical formulations comprising the composition comprising an effective amount of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion.

Also provided herein are nutraceutical compositions comprising the composition comprising an effective amount of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient.

Also provided herein are nutraceutical formulations comprising the composition comprising an effective amount of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the composition comprises an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the composition comprises an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject. In embodiments, the composition comprises an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the composition comprises an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the composition for treating a disorder or a disease associated with or characterized by neuro-inflammation, neuro-apoptosis, or neuro-oxidative damage in a subject comprises a combination of active ingredients of the herbal extract mixture prepared by extracting the herbal combination of *Paeonia japonica* and *Uncariae Ramulus* using a solvent. In embodiments, the solvent is an inorganic solvent or an organic solvent. In preferred embodiments, the solvent is water.

In embodiments, the composition for treating a disorder or a disease associated with or characterized by neuro-inflammation, neuro-apoptosis, or neuro-oxidative damage in a subject comprises a combination of active ingredients of the herbal extract mixture prepared by extracting the herbal combination of *Atractylodis Rhizoma, Cnidii Rhizoma, Paeonia japonica, Poria cocos* Wolf, *Uncariae Ramulus* Et Uncus, and *Zizyphi Semen* using a solvent. In embodiments, the solvent is an inorganic solvent or an organic solvent. In preferred embodiments, the solvent is water.

In embodiments, the composition for treating a disorder or a disease associated with or characterized by neuro-inflammation, neuro-apoptosis, or neuro-oxidative damage in a subject comprises a combination of active ingredients of the herbal extract mixture prepared by extracting the herbal combination of *Paeonia japonica, Uncariae Ramulus* Et Uncus, and *Machilus thunbergii* using a solvent. In embodiments, the solvent is an inorganic solvent or an organic solvent. In preferred embodiments, the solvent is water.

In embodiments, the composition for treating a disorder or a disease associated with or characterized by neuro-inflammation, neuro-apoptosis, or neuro-oxidative damage in a subject comprises a combination of active ingredients of the herbal extract mixture prepared by extracting the herbal combination of *Uncariae Ramulus, Paeonia japonica, Machilus thunbergii, Panax ginseng* C. A Meyer, *Glycyrrhiza uralensis, Mucunae caulis* and black pepper using a solvent. In embodiments, the solvent is an inorganic solvent or an organic solvent. In embodiments, the solvent is water.

In embodiments, the composition for treating a disorder or a disease associated with or characterized by neuro-inflammation, neuro-apoptosis, or neuro-oxidative damage in a subject comprises a combination of active ingredients of the herbal extract mixture prepared by mixing a combination of active ingredients of an herbal extract of *Paeonia japonica* and active ingredients of an herbal extract of *Uncariae Ramulus*. In embodiments, the composition for treating a disorder or a disease associated with or characterized by neuro-inflammation, neuro-apoptosis, or neuro-oxidative damage in a subject comprises a combination of active ingredients of the herbal extract mixture prepared by mixing a combination of active ingredients of an herbal extract of *Atractylodis Rhizoma*, active ingredients of an herbal extract of *Cnidii Rhizoma*, active ingredients of an herbal extract of *Paeonia japonica*, active ingredients of an herbal extract of *Poria cocos* Wolf, active ingredients of an herbal extract of *Uncariae Ramulus* Et Uncus, and active ingredients of an herbal extract of *Zizyphi Semen*. In embodiments, the composition for treating a disorder or a disease associated with or characterized by neuro-inflammation, neuro-apoptosis, or neuro-oxidative damage in a subject comprises a combination of active ingredients of the herbal extract mixture prepared by mixing a combination of active ingredients of an herbal extract of *Paeonia japonica*, active ingredients of an herbal extract of *Uncariae Ramulus* Et Uncus, and active ingredients of an herbal extract of *Machilus thunbergii*. In embodiments, the composition for treating a disorder or a disease associated with or characterized by neuro-inflammation, neuro-apoptosis, or neuro-oxidative damage in a subject comprises a combination of active ingredients of the herbal extract mixture prepared by mixing a combination of active ingredients of an herbal extract of *Uncariae Ramulus*, active ingredients of an herbal extract of *Paeonia japonica*, active ingredients of an herbal extract of *Machilus thunbergii*, active ingredients of an herbal extract of *Panax ginseng* C. A Meyer, active ingredients of an herbal extract of *Glycyrrhiza uralensis*, active ingredients of an herbal extract of *Mucunae caulis*, and active ingredients of an herbal extract of black pepper. In embodiments, the herbal extract from each herb is prepared by extracting the herb using a solvent. In embodiments, the solvent is an inorganic solvent or an organic solvent. In embodiments, the solvent is water.

Also provided herein are pharmaceutical compositions comprising the composition comprising an effective amount of a combination of active ingredients of a combination of active ingredients of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient. In embodiments, the pharmaceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, and a pharmaceutically acceptable excipient.

Also provided herein are pharmaceutical formulations comprising the composition comprising an effective amount of a combination of active ingredients of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the pharmaceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion.

Also provided herein are nutraceutical compositions comprising the composition comprising an effective amount of a combination of active ingredients of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient. In embodiments, the nutraceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, and a nutraceutically acceptable excipient.

Also provided herein are nutraceutical formulations comprising the composition comprising an effective amount of a combination of active ingredients of an herbal extract mixture to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the nutraceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of a disorder or a disease associated with or characterized by neuro-inflammation, neuro-apoptosis, or neuro-oxidative damage in a subject, wherein the composition is formulated in a form of a powder, a granule, a tablet, a pill, a capsule, a dragee, a solution, a suspension, an acupunctural needle, a gel, a syrup, a slurry, a suspension, or an emulsion.

Also provided herein in are methods of treating a disorder or a disease associated with or characterized by neuro-inflammation, neuro-apoptosis, or neuro-oxidative damage in a subject. In embodiments, the method includes the step of administering to the subject in need thereof a composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the method includes the step of administering to the subject in need thereof a pharmaceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a pharmaceutically acceptable excipient.

In embodiments, the method includes the step of administering to the subject in need thereof a pharmaceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a nutraceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a nutraceutically acceptable excipient.

In embodiments, the method includes the step of administering to the subject in need thereof a nutraceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Atractylodis Rhizoma, Cnidii Rhizoma, Paeonia japonica, Poria cocos* Wolf *Uncariae Ramulus* Et Uncus, and *Zizyphi Semen* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the method includes the step of administering to the subject in need thereof a pharmaceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a pharmaceutically acceptable excipient.

In embodiments, the method includes the step of administering to the subject in need thereof a pharmaceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a nutraceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer,

*Glycyrrhiza uralensis, Mucunae caulis* and black pepper to reduce, alleviate, ameliorate, attenuate or delay a sign or a symptom of the disorder or the disease in the subject, and a nutraceutically acceptable excipient.

In embodiments, the method includes the step of administering to the subject in need thereof a nutraceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

Also provided herein in are methods of reducing, alleviating, ameliorating, attenuating or delaying a sign or a symptom of a disorder or a disease associated with or characterized by neuro-inflammation, neuro-apoptosis, or neuro-oxidative damage in a subject. In embodiments, the method includes the step of administering to the subject in need thereof a composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Atractylodis Rhizoma, Cnidii Rhizoma, Paeonia japonica, Poria cocos* Wolf *Uncariae Ramulus* Et Uncus, and *Zizyphi Semen* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the method includes the step of administering to the subject in need thereof a pharmaceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a pharmaceutically acceptable excipient.

In embodiments, the method includes the step of administering to the subject in need thereof a pharmaceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a nutraceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a nutraceutically acceptable excipient.

In embodiments, the method includes the step of administering to the subject in need thereof a nutraceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the method includes the step of administering to the subject in need thereof a pharmaceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf *Uncariae Ramulus* Et Uncus, and *Zizyphi Semen* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a pharmaceutically acceptable excipient.

In embodiments, the method includes the step of administering to the subject in need thereof a pharmaceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a nutraceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a nutraceutically acceptable excipient.

In embodiments, the method includes the step of administering to the subject in need thereof a nutraceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

Also provided herein in are methods of regulating inflammation, antioxidant enzymes, and apoptosis in a subject having a disorder or a disease associated with or characterized by neuro-inflammation, neuro-apoptosis, or neuro-oxidative damage. In embodiments, the method includes the step of administering to the subject in need thereof a composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the method includes the step of administering to the subject in need thereof a composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the method includes the step of administering to the subject in need thereof a pharmaceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a pharmaceutically acceptable excipient.

In embodiments, the method includes the step of administering to the subject in need thereof a pharmaceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi*

*Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a nutraceutical composition comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of an herbal extract mixture of an herbal combination of *Uncariae Ramulus, Paeonia japonica, Machilus thunbergii, Panax ginseng* C. A. Meyer, *Glycyrrhiza uralensis, Mucunae caulis* and black pepper to reduce, alleviate, ameliorate, attenuate or delay a sign or a symptom of the disorder or the disease in the subject, and a nutraceutically acceptable excipient.

In embodiments, the method includes the step of administering to the subject in need thereof a nutraceutical formulation comprising the composition comprising an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the method includes the step of administering to the subject in need thereof a composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject.

In embodiments, the method includes the step of administering to the subject in need thereof a pharmaceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf *Uncariae Ramulus* Et Uncus, and *Zizyphi Semen* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a pharmaceutically acceptable excipient. In embodiments, the method includes the step of administering to the subject in need thereof a pharmaceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a pharmaceutically acceptable excipient.

In embodiments, the method includes the step of administering to the subject in need thereof a pharmaceutical formulation comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a pharmaceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, the method includes the step of administering to the subject in need thereof a nutraceutical composition comprising the composition comprising an effective amount of a combination of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Atractylodis Rhizoma, Cnidii Rhizoma, Paeonia japonica, Poria cocos* Wolf, *Uncariae Ramulus* Et Uncus, and *Zizyphi Semen* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, and a nutraceutically acceptable excipient. In embodiments, the method includes the step of administering to the subject in need thereof a nutraceutical composition comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, and a nutraceutically acceptable excipient.

In embodiments, the method includes the step of administering to the subject in need thereof a nutraceutical formulation comprising the composition comprising an effective amount of a combination of active ingredients of an herbal extract mixture of an herbal combination of *Paeonia*

*japonica* and *Uncariae Ramulus* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Atractylodis Rhizoma, Cnidii Rhizoma, Paeonia japonica, Poria cocos* Wolf; *Uncariae Ramulus* Et Uncus, and *Zizyphi Semen* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion. In embodiments, the method includes the step of administering to the subject in need thereof a nutraceutical formulation comprising the composition comprising an effective amount of a combination of active ingredients of an herbal extract mixture of an herbal combination of *Uncariae Ramulus, Paeonia japonica, Machilus thunbergii, Panax ginseng* C. A Meyer, *Glycyrrhiza uralensis, Mucunae caulis* and black pepper to reduce, alleviate, ameliorate, attenuate or delay a sign or a symptom of the disorder or the disease in the subject, wherein the composition is formulated in a form of a powder, a granule, a tablet, a pill, a capsule, a dragee, a solution, a suspension, an acupunctural needle, a gel, a syrup, a slurry, a suspension, or an emulsion.

In embodiments, in the methods of treating a disorder or a disease associated with or characterized by neuro-inflammation, neuro-apoptosis, or neuro-oxidative damage in a subject, the methods of reducing, alleviating, ameliorating, attenuating or delaying a sign or a symptom of a disorder or a disease associated with or characterized by neuro-inflammation, neuro-apoptosis, or neuro-oxidative damage in a subject, or the methods of regulating inflammation, antioxidant enzymes, and apoptosis in a subject having a disorder or a disease associated with or characterized by neuro-inflammation, neuro-apoptosis, or neuro-oxidative damage, the compositions, the pharmaceutical compositions, the pharmaceutical formulations, the nutraceutical compositions, or the nutraceutical formulations are administered by oral administration, acupunctural injection, intravenous injection, or a combination thereof. In embodiments, the compositions, the pharmaceutical compositions, the pharmaceutical formulations, the nutraceutical compositions, or the nutraceutical formulations are administered in one or more doses. In embodiments, one or more doses of the compositions, the pharmaceutical compositions, the pharmaceutical formulations, the nutraceutical compositions, or the nutraceutical formulations are delivered via a same route. In embodiments, one or more doses of the compositions, the pharmaceutical compositions, the pharmaceutical formulations, the nutraceutical compositions, or the nutraceutical formulations are delivered via different routes.

In embodiments, the methods of treating a disorder or a disease associated with or characterized by neuro-inflammation, neuro-apoptosis, or neuro-oxidative damage in a subject, the methods of reducing, alleviating, ameliorating, attenuating or delaying a sign or a symptom of a disorder or a disease associated with or characterized by neuro-inflammation, neuro-apoptosis, or neuro-oxidative damage in a subject, or the methods of regulating inflammation, antioxidant enzymes, and apoptosis in a subject having a disorder or a disease associated with or characterized by neuro-inflammation, neuro-apoptosis, or neuro-oxidative damage further includes the step of administering a secondary therapeutic regimen, agent, or treatment for treating a disorder or a disease associated with or characterized by neuro-inflammation, neuro-apoptosis, or neuro-oxidative damage in a subject, for reducing, alleviating, ameliorating, attenuating or delaying a sign or a symptom of a disorder or a disease associated with or characterized by neuro-inflammation, neuro-apoptosis, or neuro-oxidative damage in a subject, or for regulating inflammation, antioxidant enzymes, and apoptosis in a subject having a disorder or a disease associated with or characterized by neuro-inflammation, neuro-apoptosis, or neuro-oxidative damage, in conjunction with the compositions, the pharmaceutical compositions, the pharmaceutical formulations, the nutraceutical compositions, or the nutraceutical formulations simultaneously, previously, or subsequently. In embodiments, the secondary therapeutic regimen, agent, or treatment is levodopa.

Also provides herein are methods of preparing compositions, pharmaceutical compositions, pharmaceutical formulations, nutraceutical compositions, and nutraceutical formulations for treating a disorder or a disease associated with or characterized by neuro-inflammation, neuro-apoptosis, or neuro-oxidative damage in a subject. In embodiments, the compositions, the pharmaceutical compositions, the pharmaceutical formulations, the nutraceutical compositions, and the nutraceutical formulations are prepared by using the herbal extract mixture prepared by extracting herbal combinations using a solvent. In embodiments, the solvent is an inorganic solvent or an organic solvent. In preferred embodiments, the solvent is water. In embodiments, the compositions, the pharmaceutical compositions, the pharmaceutical formulations, the nutraceutical compositions, and the nutraceutical formulations are prepared by a combination of active ingredients of the herbal extract mixture prepared by extracting herbal combinations using a solvent. In embodiments, the solvent is an inorganic solvent or an organic solvent. In preferred embodiments, the solvent is water. In embodiments the compositions, the pharmaceutical compositions, the pharmaceutical formulations, the nutraceutical compositions, and the nutraceutical formulations are prepared by using the herbal extract mixture prepared by mixing a combination of an herbal extract of each herb. In embodiments the compositions, the pharmaceutical compositions, the pharmaceutical formulations, the nutraceutical compositions, and the nutraceutical formulations are prepared by mixing a combination of active ingredients of an herbal extract of each herb.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 5A and 5B shows effects of H1 and H2 on inflammation-related responses (FIG. 5A) and apoptotic signaling cascades (FIG. 5B) in MPTP-treated mice. Protein extracts from brain tissues in different groups were subjected to western blotting analysis. Results are expressed as mean±SD. Values not sharing a common superscript (a, b, c, d, and e) differed significantly (Duncan's multiple range test) ($p<0.05$).

FIG. 11 shows synergistic effects of oral administration (OM) and acupunctural injection (A) of Hepad s7 (Hs7) combined with levodopa (L) on inflammation-related responses in 1-methyl-1,2,3,6-tetrahydropyridine (MPTP)-treated rats. Protein extracts from midbrain tissues in each of the different groups were subjected to Western blotting analyses. Results are expressed as the mean±the standard deviation. The one-way ANOVA was used to determine the differences between the means. Level of statistical significance for a, b, c, d, e, and f is $p<0.05$ (Duncan's multiple range test). "L" indicates levodopa treatment; "OM" indicates oral administration of Hs7; and "A" indicates acupunctural injection (I.V. injection) of Hs7.

DETAILED DESCRIPTION OF THE DISCLOSURE

Figure 1A:
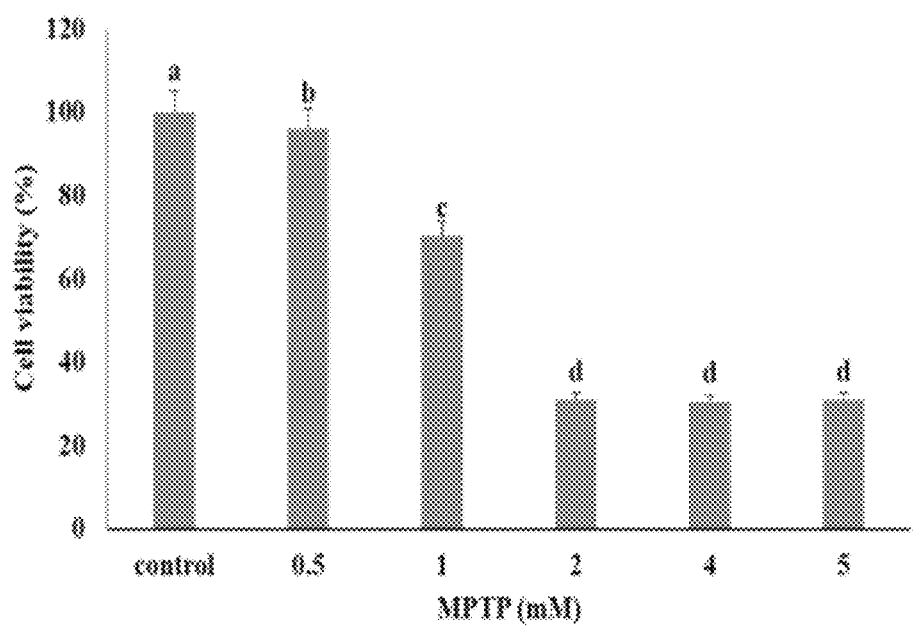
FIGS. 1A-1C show that Hepad 1 (H1) and Hepad 2 (H2) inhibit 1-methyl-4-phenyl-1,2,3,6-tetrahydropyridine (MPTP)-induced cell death in SH-SY5Y cells. SH-SY5Y cells ($2\times10^6$) were incubated in the absence or presence of MPTP for 24 h (FIG. 1A). SH-SY5Y cells were pre-treated with 1 mM (FIG. 1B) and 2 mM (FIG. 1C) MPTP for 4 h. The cells were then incubated with 200, 500, and 700 μg/mL of H1 and H2 for 24 h. Subsequently, the survival rate was measured by 3-(4,5-dimethylthiazol-2-yl)-2,5-diphenyltetrazolium bromide assay. The data are expressed as the relative ratio to the absorbance of the untreated cells, which was set at 100%, and are reported as mean±SD of three independent experiments. Results are expressed as mean±SD. Values not sharing a common superscript (a, b, c, d, and e) differed significantly (Duncan's multiple range test) ($p<0.05$).

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention can be described in the context of a single embodiment, the features can also be provided separately or in any suitable combination. Conversely, although the invention can be described herein in the context of separate embodiments for clarity, the invention can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

The terms "subject" and "patient," as used herein, include animals (e.g., vertebrates, amphibians, fish, mammals, cats, dogs, horses, pigs, cows, sheep, rodents, rabbits, squirrels, bears, primates (e.g., chimpanzees, gorillas, and humans)), which are capable of suffering from a disease or a disorder associated with or characterized by neuro-inflammation, neuro-apoptosis, or neuro-oxidative damage. "Subject" may also be a cell, a population of cells, a tissue, an organ, or an organism, preferably to human and constituents thereof. The subject is preferably a mammal in need of such treatment, e.g., a subject that has been diagnosed with or has a risk of or have a predisposition of developing a disorder associated with or characterized by neuro-inflammation, neuro-apoptosis, or neuro-oxidative damage. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

A "control" or "standard control" refers to a sample, measurement, or value that serves as a reference, usually a known reference, for comparison to a test sample, measurement, or value. For example, a test sample can be taken from a subject having a given disease PD) and compared with a known normal (non-diseased) individual (e.g., a standard control subject). A standard control can also represent an average measurement or value gathered from a population of similar individuals (e.g., standard control subjects) that do not have a given disease (i.e., standard control population), e.g., healthy individuals with a similar medical background, same age, weight, etc. A standard control value can also be obtained from the same individual, e.g., from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g., RNA levels, protein levels, specific cell types, specific bodily fluids, specific tissues, brain tissue, etc).

"Sham" surgery or procedure (placebo surgery or procedure) is a faked surgical intervention or procedure that omits the step thought to be therapeutically necessary. Sham surgery or procedure is an important control, because it isolates the specific effects of the treatment as opposed to the incidental effects caused by anesthesia, the incisional trauma, pre- and postoperative care, and the subject's perception of having had a regular operation. Sham surgery or procedure serves an analogous purpose to placebo drugs, neutralizing biases such as the placebo effect.

The terms "prevent," "preventing," and "prevention," as used herein, refer to a decrease in the occurrence of pathology of a disease or a disorder associated with or characterized by neuro-inflammation, neuro-apoptosis, or neuro-oxidative damage in a subject. The prevention may be complete, e.g., the total absence of pathology of a disease or a disorder associated with or characterized by neuro-inflammation, neuro-apoptosis, or neuro-oxidative damage in a subject. The prevention may also be partial, such that the occurrence of pathology a disease or a disorder associated with or characterized by neuro-inflammation, neuro-apoptosis, or neuro-oxidative damage in a subject is less than that which would have occurred without the present invention.

The terms "treat," "treating", and "treatment," and the like are used herein to generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly, a human, and includes: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions. The invention is directed towards treating a patient's suffering from a disease or a disorder associated with or characterized by neuro-inflammation, neuro-apoptosis, or neuro-oxidative damage. The term "prophylaxis" is used herein to refer to a measure or measures taken for the prevention or partial prevention of a disease or condition.

By "treating or preventing a disease or a disorder associated with or characterized by neuro-inflammation, neuro-apoptosis, or neuro-oxidative damage" is meant ameliorating any of the conditions or signs or symptoms associated with the disorder before or after it has occurred including, for example, neuronal cell death, inflammation, oxidative stress, and motor deficits. For example, alleviating a symptom of a disorder may involve reducing visible areas of neuronal cell death relative to an untreated control. As compared with an equivalent untreated control, such reduction or degree of prevention is at least 3%, 5%, 10%, 20%, 40%, 50%, 60%, 80%, 90%, 95%, or 100% as measured by any standard technique. A patient who is being treated for a disease or a disorder associated with or characterized by neuro-inflammation, neuro-apoptosis, or neuro-oxidative damage, for example, a neurological disease, is one who a medical practitioner has diagnosed as having such a condition. Diagnosis may be by any suitable means. Diagnosis and monitoring may involve, for example, detecting the presence of destroyed or dying neurons in a biological sample (e.g., tissue biopsy, blood test, or urine test), detecting the presence of plaques, detecting the level of a surrogate marker of the neurologic disorder in a biological sample, or detecting symptoms associated with the neurologic disorder. A patient in whom the development of a neurologic disorder is being prevented may or may not have received such a diagnosis. One in the art will understand that these patients may have been subjected to the same standard tests as described above or may have been identified, without examination, as one at high risk due to the presence of one or more risk factors (e.g., family history or genetic predisposition).

The therapeutic methods of the invention may be carried out on subjects displaying pathology resulting from a disease or a disorder associated with or characterized by neuro-inflammation, neuro-apoptosis, or neuro-oxidative damage, for example, PD, subjects suspected of displaying pathology resulting from PD, and subjects at risk of displaying pathology resulting from PD. For example, subjects that have a genetic predisposition to PD can be treated prophylactically. Subjects exhibiting PD symptoms may be treated to decrease the symptoms or to slow down or prevent further progression of the symptoms. The physical changes associated with the increasing severity of PD are shown herein to be progressive. Thus, in embodiments of the invention, subjects exhibiting mild signs of PD pathology may be treated to improve the symptoms and/or prevent further progression of the symptoms.

The term "synergistic," as used herein, refers to an effect obtained when a first agent and a second agent are administered together (e.g., at the same time or one after the other) that is greater than the additive effect of the first agent and the second agent when administered individually. The synergistic effect allows for lower doses of the first agent and/or the second agent to be administered or provides greater efficacy at the same doses. The synergistic effect obtained can be at least 10%, at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, at least 350%, at least 400%, or at least 500% more than the additive effect of the first agent and the second agent when administered individually.

PD is caused by a deficiency of neurotransmitter dopamine at the nerve terminals of nigrostriatal dopaminergic neurons in the striatum because of the selective loss of dopaminergic neurons in the substantia nigra pars compacta (SNpc). PD is characterized by motor dysfunctions, such as bradykinesia, rigidity of the limbs, and shuffling gaits. The factors that are speculated to contribute to the mechanism underlying the pathogenesis of PD include disturbances of intracellular calcium homeostasis, exogenous and endogenous toxins, mitochondrial dysfunction, cell death of the nigrostriatal dopaminergic neurons, oxidative stress, and cytotoxicity of reactive oxygen spices. These factors are predicted to constitute a complex network that leads to the dopaminergic neuronal cell death of PD.

Neurodegenerative processes are generally characterized by a long-lasting course of neuronal death. Apoptosis is a programmed cell death and is characterized by morphological changes, including cell shrinkage, nuclear condensation, and DNA degradation. The apoptotic process is caused by a cascade of events, in which a family of cysteine proteases known as caspases mediates the cleavage of multiple cellular substrates. The apoptotic death is characterized by altered expression of genes, the majority of which are oncogenes. Some oncogenes enhance the apoptotic process (BCL2 associated X (bax) and B-cell lymphoma (bcl)-x), but others inhibit the death process (bcl-2 and bcl-xL). In addition, the necrotizing cell swelling and rupture provoke an inflammatory response.

Neuroinflammation also contributes to neurodegeneration and is thought to be mainly associated with overactive glial cells in the brains of PD patients. Microglial cells, which are resident macrophages in the brain, synthesize inflammatory factors, such as cyclooxygenase-2 (COX-2), tumor necrosis factor-α (TNF-α), and interleukin-6 (IL-6). These inflammatory factors are responsible for neuroglia-mediated neuroinflammation and neurotoxicity.

Compositions Comprising Herbal Extracts

Provided herein are compositions for treating diseases or disorders associated with or characterized by neuro-inflammation, neuro-apoptosis, or neuro-oxidative damage. The diseases or disorders associated with or characterized by neuro-inflammation, neuro-apoptosis, or neuro-oxidative damage are, preferably, neurological diseases. The diseases or disorders associated with or characterized by neuro-inflammation, neuro-apoptosis, or neuro-oxidative damage are, more preferably, neurodegenerative diseases. The diseases or disorders associated with or characterized by neuro-inflammation, neuro-apoptosis, or neuro-oxidative damage are, more preferably, aging-associated neurodegenerative disease. The diseases or disorders associated with or characterized by neuro-inflammation, neuro-apoptosis, or neuro-oxidative damage are, most preferably, PD.

In embodiments, the composition for treating a disorder or a disease associated with or characterized by neuro-inflammation, neuro-apoptosis, or neuro-oxidative damage is an herbal medicine for the treatment of PD. In embodiments, the composition for treating a disorder or a disease associated with or characterized by neuro-inflammation, neuro-apoptosis, or neuro-oxidative damage comprises an effective amount of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the composition for treating a disorder or a disease associated with or characterized by neuro-inflammation, neuro-apoptosis, or neuro-oxidative damage comprises an effective amount of an herbal extract mixture of an herbal combination of *Atractylodis Rhizoma, Cnidii Rhizoma, Paeonia japonica, Poria cocos* Wolf *Uncariae Ramulus Et Uncus*, and *Zizyphi Semen* to reduce, alleviate, ameliorate, attenuate or delay a sign or a symptom of the disorder or the disease in the subject. In embodiments, the composition for treating a disorder or a disease associated with or characterized by neuro-inflammation, neuro-apoptosis, or neuro-oxidative damage comprises an effective amount of an herbal extract mixture of an herbal combination of *Paeonia japonica, Uncariae Ramulus Et Uncus*, and *Machilus thunbergii* to reduce, alleviate, ameliorate, attenuate or delay a sign or a symptom of the disorder or the disease in the subject. In embodiments, the composition for treating a disorder or a disease associated with or characterized by neuro-inflammation, neuro-apoptosis, or neuro-oxidative damage comprises an effective amount of an herbal extract mixture of an herbal combination of *Uncariae Ramulus* (or *Uncariae Ramulus* et Uncus or *Uncaria rhynchophylla*), *Paeonia japonica* (or Ranunculaceae or *Paeonia obovate* or Paeoniae Radix Alba), *Machilus thunbergii*, (or *Magnolia officinalis* or a stem bark of *Machilus thunbergii* S.), *Panax ginseng* C. A Meyer, *Glycyrrhiza uralensis* (or Glycyrrhizae Radix, roots and stolons), *Mucunae Caulis* (or *Spatholobi Caulis*) and black pepper (or *Piperis Nigri Fructus*) to reduce, alleviate, ameliorate, attenuate or delay a sign or a symptom of the disorder or the disease in the subject.

In embodiments, the composition for treating a disorder or a disease associated with or characterized by neuro-inflammation, neuro-apoptosis, or neuro-oxidative damage comprises an effective amount of active ingredients of an herbal extract mixture of an herbal combination of *Paeonia japonica* and *Uncariae Ramulus* to reduce, alleviate, ameliorate, attenuate or delay a sign or a symptom of the disorder or the disease in the subject. In embodiments, the composition for treating a disorder or a disease associated with or characterized by neuro-inflammation, neuro-apoptosis, or neuro-oxidative damage comprises an effective amount of active ingredients of an herbal extract mixture of an herbal combination of *Atractylodis Rhizoma, Cnidii Rhizoma, Paeonia japonica, Poria cocos* Wolf *Uncariae Ramulus* Et Uncus, and *Zizyphi Semen* to reduce, alleviate, ameliorate, attenuate or delay a sign or a symptom of the disorder or the disease in the subject. In embodiments, the composition for treating a disorder or a disease associated with or characterized by neuro-inflammation, neuro-apoptosis, or neuro-oxidative damage comprises an effective amount of active ingredients of an herbal extract mixture of an herbal combination of *Paeonia japonica, Uncariae Ramulus* Et Uncus, and *Machilus thunbergii* to reduce, alleviate, ameliorate, attenuate or delay a sign or a symptom of the disorder or the disease in the subject. In embodiments, the composition for treating a disorder or a disease associated with or characterized by neuro-inflammation, neuro-apoptosis, or neuro-oxidative damage comprises an effective amount of active ingredients of an herbal extract mixture of an herbal combination of *Uncariae Ramulus* (or *Uncariae Ramulus* et Uncus or *Uncaria rhynchophylla*), *Paeonia japonica* (or Ranunculaceae or *Paeonia obovate* or Paeoniae Radix Alba), *Machilus thunbergii*, (or *Magnolia officinalis* or a stem bark of *Machilus thunbergii* S.), *Panax ginseng* C. A Meyer, *Glycyrrhiza uralensis* (or Glycyrrhizae Radix, roots and stolons), *Mucunae Caulis* (or *Spatholobi Caulis*) and black pepper (or *Piperis Nigri Fructus*) to reduce, alleviate, ameliorate, attenuate or delay a sign or a symptom of the disorder or the disease in the subject.

In embodiments, the composition for treating a disorder or a disease associated with or characterized by neuro-inflammation, neuro-apoptosis, or neuro-oxidative damage comprises one or more additional herbal extracts or active ingredients of one or more additional herbal extracts. Examples of additional herbal extracts include, but are not limited to, Arecae Semen (or *Areca catechu*) extract, Rubiae Radix (or *Senecio radicans*) extract, *Lycii Fructus* extract, *Kochiae Fructus* extract, *Schizandrae Fructus* (or *Schisandra chinensis*) extract, *Arisamatis Rhizoma* extract, *Pinellia ternate* (or Pinelliae Rhizoma) extract, *Astragali Radix* (or *Astragalus mongholicus* var. *dahuricus* (DC.) Podlech) extract, *Atractylodis Rhizoma* White extract, Scrophulariae Radix (or *Scrophularia buergeriana*) extract, *Cinnamomi Ramulus* extract, *Cinnamomum cassia* (or *Cinnamomum loureiroi, Cinnamomum verum, Cinnamomum burmannii*) extract, *Aconiti Koreani* Tuber (or *Aconitum variegatum*) extract, *Aconiti Ciliare* Tuber extract, Angelicae Gigantis Radix (or *Angelica gigas*) extract, *Cnidii Rhizoma* (or *Cnidium officinale*) extract, Rehmanniae Radix Preparat (or *Rehmannia glutinosa*) extract, Dioscoreae Rhiozoma (or *Dioscorea japonica*) extract, Corni *Fructus* (or *Cornus officinalis*) extract, *Amomi Rotundus Fructus* extract, Myristicae Semen extract, Cuscutae Semen extract, *Rubi Fructus* (or *Rubus coreanus*) extract, *Cinnamomi* Cortex (or *Cinnamomum cassia*) extract, *Ziziphus jujuba* extract, *Cervi Parvum Cornu* extract, *Cervi Cornus Degelatinatum* extract, *Raphani Semen* extract, Ephedrae Radix (or *Ephedra distachya, Ephedra sinica*) extract, *Cnidii Fructus* (or *Torilis japonica*) extract, and *Asini Gelatinum* extract.

The weight ratio of each component of the composition of the invention ranges from 1 to 100 and any integer values in between. For example, in H1, the ratio of *Atractylodis Rhizoma:Cnidii Rhizoma:Paeonia japonica:Poria cocos* Wolf: *Uncariae Ramulus* Et Uncus:*Zizyphi Semen* is 1-100 and any integer value in between:1-100 and any integer value in between:1-100 and any integer value in between: 1-100 and any integer value in between:1-100 and any integer value in between:1-100 and any integer value in between, based on the weight of each component. In embodiments, the ratio of *Atractylodis Rhizoma:Cnidii Rhizoma:Paeonia japonica:Poria cocos* Wolf: *Uncariae Ramulus* Et Uncus:*Zizyphi Semen* of H1 is, preferably, 1:1:1:1:1:1, based on the weight of each component. For another example, in H2, the ratio of *Paeonia japonica:Uncariae Ramulus* Et Uncus:*Machilus thunbergii* is 1-500 and any integer value in between:1-500 and any integer value in between:1-500 and any integer value in between, based on the weight of each component. In embodiments, the ratio of *Paeonia japonica:Uncariae Ramulus* Et Uncus:*Machilus thunbergii* of H2 is, preferably, 1:1:1, based on the weight of each component. For another example, in Hs7, the ratio of *Uncariae Ramulus:Paeonia japonica:Machilus thunbergii: Panax ginseng* C. A Meyer: *Glycyrrhiza uralensis:Mucunae caulis*:black pepper is 1-500 and any integer value in between:1-500 and any integer value in between:1-500 and any integer value in between:1-500 and any integer value in between:1-500 and any integer value in between:1-500 and any integer value in between:1-500 and any integer value in between, based on the weight of each component. In embodiments, the ratio of the ratio of *Uncariae Ramulus: Paeonia japonica:Machilus thunbergii:Panax ginseng* C. A Meyer:*Glycyrrhiza uralensis:Mucunae caulis*:black pepper of Hs7 is, preferably, 1:1:1:1:1:1:1, based on the weight of each component.

The composition for treating diseases or disorders associated with or characterized by neuro-inflammation, neuro-apoptosis, or neuro-oxidative damage, as described herein, is prepared by obtaining herbal extracts by wetting, soaking, simmering or boiling herbs in inorganic solvents or organic solvents for time duration to sufficiently extract ingredients for treating diseases or disorders associated with or characterized by neuro-inflammation, neuro-apoptosis, or neuro-oxidative damage. Examples of inorganic solvents and organic solvents include, but are not limited to, water and the like, alcohols, such as C1-C8 alcohols including methanol, ethanol, propanol, butanol, and the like, organic acids including acetic acid, formic acid, propanoic acid, and the like, polyols and glycols including C1-C8 polyols/glycols and the like, alkanes including C1-C8 alkanes, cycloalkanes, alkyl ethers including C1-C8 alkyl ethers, petroleum ethers, ketones including C1-C8 ketones, methylene chloride, ethyl acetate, xylene, toluene, chloroform, vegetable oil, mineral oil and the like, and combinations of two or more thereof. In preferred embodiments, the composition is prepared using water.

In embodiments, herbs are wetted, soaked, simmered or boiled for 5 min, 10 min, 15 min, 20 min, 25 min, 30 min, 40 min, 50 min, 60 min, 2 hours (hrs), 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, 2 days, 3 days 4 days, 5 days, 6 days, or 7 days. In embodiments, the herbs are extracted in boiling water. In preferred embodiments, the herbs are extracted in boiling water for 24 hrs.

In embodiments, the herbal extracts are further processed. In embodiments, the herbal extracts are filtered. In embodiments, the herbal extracts are filtered to remove debris, remains or pulps of the herbs. In embodiments, the herbal extracts are concentrated. In embodiments, the herbal extracts are concentrated under reduced pressure. In embodiments, the herbal extracts are concentrated at 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C. In embodiments, the herbal extracts are concentrated under reduced pressure at 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C. In preferred embodiments, the herbal extracts are concentrated under reduced pressure at 50° C. In embodiments, the herbal extracts are filtered and concentrated. In embodiments, the herbal extracts are filtered and concentrated under reduced pressure. In embodiments, the herbal extracts are filtered and concentrated at 50° C. In preferred embodiments, the herbal extracts are filtered and concentrated under reduced pressure at 50° C.

In embodiments, the composition is prepared by mixing a combination of herbs and obtaining an herbal extract from the combination of herbs. In embodiments, an herbal extract is prepared from each herb and the composition is prepared by mixing a combination of herbal extracts prepared from each herb. In embodiments, the herbal extract prepared from each herb is further processed, for example, filtered and/or concentrated, and then, a combination of the processed herbal extracts prepared from each herb is mixed. In embodiments, a combination of the herbal extracts prepared from each herb is mixed and the mixed combination of the herbal extracts is further processed, for example, filtered and/or concentrated.

Therapeutic Applications

Also provided herein are methods of treating a disease or a disorder associated with or characterized by neuro-inflammation, neuro-apoptosis, or neuro-oxidative damage, methods of reducing, alleviating, ameliorating, attenuating or delaying a sign or a symptom of a disorder or a disease associated with or characterized by neuro-inflammation, neuro-apoptosis, or neuro-oxidative damage in a subject, and methods of regulating inflammation, antioxidant enzymes, and apoptosis in a subject having a disorder or a disease associated with or characterized by neuro-inflammation, neuro-apoptosis, or neuro-oxidative damage including the step of administering the composition comprising herbal extracts as described herein.

In embodiments, a disease or a disorder associated with or characterized by neuro-inflammation, neuro-apoptosis, or neuro-oxidative damage is a neurological disease. In embodiments, a disease or a disorder associated with or characterized by neuro-inflammation, neuro-apoptosis, or neuro-oxidative damage is a neurodegenerative disease. In preferred embodiments, a disease or a disorder associated with or characterized by neuro-inflammation, neuro-apoptosis, or neuro-oxidative damage is an aging-associated neurodegenerative disease, for example, Alzheimer's disease (AD), PD, amyotrophic lateral sclerosis (ALS), tauopathies, and age-related macular degeneration. In more preferred embodiments, a disease or a disorder associated with or characterized by neuro-inflammation, neuro-apoptosis, or neuro-oxidative damage is PD.

The administration of compositions described herein can be carried out in any convenient manner, including by aerosol inhalation, injection, ingestion, transfusion, implantation or transplantation. Examples of routes of administration include parenteral, e.g., intravenous or intra-arterial, intradermal, subcutaneous, oral (e.g., inhalation), transdermal (topical), transmucosal, nasal, pulmonary, ocular, gastrointestinal, and rectal administration. Alternate routes of administration include intraperitoneal, intra-articular, intracardiac, intracisternal, intradermal, intralesional, intraocular, intrapleural, intrathecal, intrauterine, intraventricular, and the like. In embodiments, the administration of compositions described herein is carried out by acupunctural injection. The term "acupunctural injection," as used herein, refers to the insertion of thin needles into the body, for example, into the skin, to inject or administer a drug, a medicine or an extract. The terms "herbal drug acupuncture" and "pharmacopuncture," as used herein, refers to the administration of an herbal drug, an herbal medicine or an herbal extract in to the body by acupunctural injection. In embodiments, the acupunctural injection of an herbal drug, an herbal medicine or an herbal extract leads to intravenous administration or injection.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Adjustment and manipulation of established dosages (e.g., frequency and duration) are well within the ability of those skilled in the art. The treatment, such as those disclosed herein, can be administered to the subject on a daily, twice daily, biweekly, monthly or any applicable basis that is therapeutically effective. In embodiments, the treatment is only on an as-needed basis, e.g., upon appearance of signs or symptoms of a disease or a disorder associated with or characterized by neuro-inflammation, neuro-apoptosis, or neuro-oxidative damage, for example, PD.

In embodiment, a subject in need thereof can begin therapy with a first dose of the composition of the invention followed by a second dose of the composition of the invention. In further embodiments, the second dose of the composition of the invention can be followed by subsequent doses. In embodiments, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours. In embodiments, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some embodiment, the duration between the first and second or further subsequent dose can be about: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In another embodiment, the duration between the first and second or further subsequent dose can be about: 0, 1, 2, 3, 4, 5, 6, 7, 8, 9 or 10 years.

In embodiments, the first dose and second or further subsequent dose are delivered via a same route, for example, oral administration, parenteral administration and acupunctural injection. In embodiments, the first dose and second or further subsequent dose are delivered via different routes. For example, in embodiments, the first dose is delivered via oral administration and the second or further subsequent dose is delivered via parenteral administration. In embodiments, the first dose is delivered via parenteral administration and the second or further subsequent dose is delivered via oral administration. In embodiments, the first dose is delivered via oral administration and the second or further subsequent dose is delivered via acupunctural injection. In embodiments, the first dose is delivered via acupunctural injection and the second or further subsequent dose is delivered via oral administration. In embodiments, the first dose is delivered via parenteral administration and the second or further subsequent dose is delivered via acupunctural injection. In embodiments, the first dose is delivered via acupunctural injection and the second or further subsequent dose is delivered via parenteral administration.

In embodiments, the first dose is delivered via oral administration, the second dose is delivered via parenteral administration, and further subsequent dose is delivered via acupunctural injection. In embodiments, the first dose is delivered via oral administration, the second dose is delivered via acupunctural injection, and further subsequent dose is delivered via parenteral administration. In embodiments, the first dose is delivered via parenteral administration, the second dose is delivered via oral administration, and further subsequent dose is delivered via acupunctural injection. In embodiments, the first dose is delivered via parenteral administration, the second dose is delivered via acupunctural injection, and further subsequent dose is delivered via oral administration. In embodiments, the first dose is delivered via acupunctural injection, the second dose is delivered via oral administration, and further subsequent dose is delivered via parenteral administration. In embodiments, the first dose is delivered via acupunctural injection, the second dose is delivered via parenteral administration, and further subsequent dose is delivered via oral administration.

For any composition described herein, the therapeutically effective amount can be initially determined from cell culture assays. Target concentrations will be those concentrations of active component(s) of the composition that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Toxicity and therapeutic efficacy of the compositions of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects (the ratio LD50/ED50) is the therapeutic index. Agents that exhibit high therapeutic indices are preferred. The dosage of agents lies preferably within a range of circulating concentrations that include the ED50 with little or no toxicity. While agents that exhibit toxic side effects may be used, care should be taken to design a delivery system that targets such agents to the site of affected tissue in order to minimize potential damage to uninfected cells and, thereby, reduce side effects.

The amount of the compound in the composition should also be in therapeutically effective amounts. The phrase "therapeutically effective amounts" used herein refers to the amount of agent needed to treat, ameliorate, or prevent a targeted disease or condition. An effective initial method to determine a "therapeutically effective amount" may be by carrying out cell culture assays (for example, using neuronal cells) or using animal models (for example, mice, rats, rabbits, dogs or pigs). A dose may be formulated in animal models to achieve a concentration range that includes the IC50 (i.e., the concentration of the composition which achieves a half-maximal inhibition of symptoms) as determined in cell culture. Such information can be used to more accurately determine useful doses in humans. In addition to determining the appropriate concentration range for an invention composition to be therapeutically effective, animal models may also yield other relevant information such as preferable routes of administration that will give maximum effectiveness. Such information may be useful as a basis for patient administration. A "patient" as used in herein refers to the subject who is receiving treatment by administration of the compound of interest.

As defined herein, a therapeutically effective amount of the composition of the invention (i.e., an effective dosage) ranges from about 0.001 to 1 g; however, amounts below or above this exemplary range are within the scope of the invention. For example, in embodiments, the composition of the invention is provided at 10 µg, 20 µg, 30 µg, 40 µg, 50 µg, 60 µg, 70 µg, 80 µg, 90 µg, 100 µg, 200 µg, 300 µg, 400 µg, 500 µg, 600 µg, 700 µg, 800 µg, 900 µg, or 1000 µg. In embodiments, the composition of the invention is provided at 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, 500 µg/ml, 600 µg/ml, 700 µg/ml, 800 µg/ml, 900 µg/ml, or 1000 µg/ml.

In embodiments, a therapeutically effective amount of the composition of the invention (i.e., an effective dosage) ranges from about 0.001 to 10,000 mg/kg body weight. In embodiments, the composition of the invention is provided at 1 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 20 mg/kg body weight, 30 mg/kg body weight, 40 mg/kg body weight, 50 mg/kg body weight, 60 mg/kg body weight, 70 mg/kg body weight, 80 mg/kg body weight, 90 mg/kg body weight, 100 mg/kg body weight, 200 mg/kg body weight, 300 mg/kg body weight, 400 mg/kg body weight, 500 mg/kg body weight, 600 mg/kg body weight, 700 mg/kg body weight, 800 mg/kg body weight, 900 mg/kg body weight, 1000 mg/kg body weight, 2000 mg/kg body weight, 3000 mg/kg body weight, 4000 mg/kg body weight, 5000 mg/kg body weight, 6000 mg/kg body weight, 7000 mg/kg body weight, 8000 mg/kg body weight, 9000 mg/kg body weight, or 10,000 mg/kg body weight.

In embodiments, a therapeutically effective amount of the composition of the invention (i.e., an effective dosage) ranges from about 0.01 to 100 ml/kg body weight. In embodiments, the composition of the invention is provided at 0.1 ml/kg body weight, 0.2 ml/kg body weight, 0.3 ml/kg body weight, 0.4 ml/kg body weight, 0.5 ml/kg body weight, 0.6 ml/kg body weight, 0.7 ml/kg body weight, 0.8 ml/kg body weight, 0.9 ml/kg body weight, 1.0 ml/kg body weight, 1.1 ml/kg body weight, 1.2 ml/kg body weight, 1.3 ml/kg body weight, 1.4 ml/kg body weight, 1.5 ml/kg body weight, 1.6 ml/kg body weight, 1.7 ml/kg body weight, 1.8 ml/kg body weight, 1.9 ml/kg body weight, 2.0 ml/kg body weight, 3.0 ml/kg body weight, 4.0 ml/kg body weight, 5.0 ml/kg body weight, 6.0 ml/kg body weight, 7.0 ml/kg body weight, 8.0 ml/kg body weight, 9.0 ml/kg body weight, 10 ml/kg body weight, 20 ml/kg body weight, 30 ml/kg body weight, 40 ml/kg body weight, 50 ml/kg body weight, 60 ml/kg body weight, 70 ml/kg body weight, 80 ml/kg body weight, 90 ml/kg body weight, or 100 ml/kg body weight.

In embodiments, a therapeutically effective amount of the composition of the invention (i.e., an effective dosage) by acupunctural injection or by herbal drug acupuncture or pharmacopuncture ranges from about 0.01 to 50 ml/kg body weight. In embodiments, the composition of the invention is provided by an acupunctural injection at 0.1 ml/kg body weight, 0.2 ml/kg body weight, 0.3 ml/kg body weight, 0.4 ml/kg body weight, 0.5 ml/kg body weight, 0.6 ml/kg body weight, 0.7 ml/kg body weight, 0.8 ml/kg body weight, 0.9 ml/kg body weight, 1.0 ml/kg body weight, 1.1 ml/kg body weight, 1.2 ml/kg body weight, 1.3 ml/kg body weight, 1.4 ml/kg body weight, 1.5 ml/kg body weight, 1.6 ml/kg body weight, 1.7 ml/kg body weight, 1.8 ml/kg body weight, 1.9 ml/kg body weight, 2.0 ml/kg body weight, 2.1 ml/kg body weight, 2.2 ml/kg body weight, 2.3 ml/kg body weight, 2.4 ml/kg body weight, 2.5 ml/kg body weight, 2.6 ml/kg body weight, 2.7 ml/kg body weight, 2.8 ml/kg body weight, 2.9 ml/kg body weight, 3.0 ml/kg body weight, 4.0 ml/kg body weight, 5.0 ml/kg body weight, 6.0 ml/kg body weight, 7.0 ml/kg body weight, 8.0 ml/kg body weight, 9.0 ml/kg body weight, 10 ml/kg body weight, 20 ml/kg body weight, 30 ml/kg body weight, 40 ml/kg body weight, or 50 ml/kg body weight.

The skilled artisan will appreciate that certain factors may influence the dosage and frequency of administration required to effectively treat a subject, including but not limited to the severity of the disease or disorder, previous treatments, the general characteristics of the subject including health, sex, weight and/or age of the subject, and other diseases present. Moreover, treatment of a subject with a therapeutically effective amount of the compositions can include a single treatment or, preferably, can include a series of treatments. It will also be appreciated that the effective dosage of the composition of the invention used for treatment may increase or decrease over the course of a particular treatment. Changes in dosage may result and become apparent from the results of diagnostic assays as described herein. The therapeutically-effective dosage will generally be dependent on the patient's status at the time of administration. The precise amount can be determined by routine experimentation but may ultimately lie with the judgment of the clinician, for example, by monitoring the patient for signs of disease and adjusting the treatment accordingly.

The methods and compositions of the invention described herein including embodiments thereof can be administered with one or more additional therapeutic regimens or agents or treatments, which can be co-administered to the mammal. By "co-administering" is meant administering one or more additional therapeutic regimens or agents or treatments and the composition of the invention sufficiently close in time to enhance the effect of one or more additional therapeutic agents, or vice versa. In this regard, the composition of the invention described herein can be administered simultaneously with one or more additional therapeutic regimens or agents or treatments, at a different time, or on an entirely different therapeutic schedule (e.g., the first treatment can be daily, while the additional treatment is weekly). For example, in embodiments, the secondary therapeutic regimens or agents or treatments are administered simultaneously, prior to, or subsequent to the composition of the invention.

In embodiments, the secondary agent can be one which is used clinically for treatment of a disease or a disorder associated with or characterized by neuro-inflammation, neuro-apoptosis, or neuro-oxidative damage, e.g., PD. In embodiments, levodopa is co-administered with the composition of the invention or is present on the same surface as the composition of the invention. Examples of the additional therapeutic regimens or agents or treatments that can be included in or co-administered with the composition include, but are not limited to, medications, such as carbidopa-levodopa, levodopa, carbidopa-levodopa infusion, dopamine agonists (e.g., pramipexole (Mirapex), ropinirole (Requip), rotigotine (Neupro), and apomorphine (Apokyn)), MAO B inhibitors (e.g., selegiline (Eldepryl, Zelapar), rasagiline (Azilect), and safinamide (Xadago)), catechol O-methyltransferase (COMT) inhibitors (e.g., entacapone (Comtan) and tolcapone (Tasmar)), anticholinergics (e.g., benztropine (Cogentin), trihexyphenidyl, amantadine); surgical procedures, such as deep brain stimulation; lifestyle and home remedies, such as healthy eating, exercise, and physical therapy; and alternative medicines, such as massage, tai chi, yoga, alexander technique, meditation and pet therapy.

Pharmaceutical and Nutraceutical Compositions

Also provided herein are pharmaceutical and nutraceutical compositions comprising the compositions for treating a disease or a disorder associated with or characterized by neuro-inflammation, neuro-apoptosis, or neuro-oxidative damage comprising herbal extract mixtures as described herein. Pharmaceutical and nutraceutical compositions described herein can comprise the composition as described herein in combination with one or more pharmaceutically or physiologically or nutraceutically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

A pharmaceutical or a nutraceutical composition used in the therapeutic methods of the invention is formulated to be compatible with its intended route of administration.

For oral administration, the compositions can be formulated in liquid or solid dosage forms and as instant or controlled/sustained release formulations. Suitable dosage forms for oral ingestion by a subject include powders, tablets, pills, granules, dragees, hard and soft shell capsules, liquids, gels, syrups, slurries, suspensions, emulsions and the like. Oral compositions generally include an inert diluent or an edible carrier. They can be enclosed in gelatin capsules or compressed into tablets. For the purpose of oral therapeutic administration, the active agent can be incorporated with excipients and used in the form of tablets, troches, or capsules. Oral compositions can also be prepared using a fluid carrier for use as a mouthwash, wherein the agent in the fluid carrier is applied orally and swished and expectorated or swallowed. Pharmaceutically or nutraceutically compatible binding agents, and/or adjuvant materials can be included as part of the composition. The tablets, granules, pills, capsules, troches and the like can contain any of the following ingredients, or compounds of a similar nature: a binder such as micro-crystalline cellulose, gum tragacanth or gelatin; an excipient such as starch or lactose; dissolution retardant; anti-adherants; cationic exchange resin; wetting agents; antioxidants; preservatives; a disintegrating agent such as alginic acid, Primogel, or corn starch; a lubricant such as magnesium stearate or Sterotes; a glidant such as colloidal silicon dioxide; a preservative; a colorant; a sweetening agent such as sugars such as dextrose, sucrose or saccharin; or a flavoring agent such as peppermint, methyl salicylate, or orange flavoring, each of these being synthetic and/or natural.

In one embodiment, the compositions are prepared with carriers that will protect the components of the composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral anti-gens) can also be used as pharmaceutically or nutraceutically acceptable carriers. These can be prepared according to methods known to those skilled in the art, for example, as described in U.S. Pat. No. 4,522,811.

The term "preparation," is intended to include the formulation of the compositions with encapsulating material as a carrier providing a capsule in which the active compositions with or without other carriers, is surrounded by a carrier, which is thus in association with it.

For administration by inhalation, the compositions are delivered in the form of an aerosol spray from pressured container or dispenser which contains a suitable propellant, e.g., a gas such as carbon dioxide, or a nebulizer. Systemic administration can also be by transmucosal or trans-dermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams, emulsion, a solution, a suspension, or a foam, as generally known in the art. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustments; use of complexing agents and other techniques, such as iontophoresis, may be used to regulate skin penetration of the active ingredient.

The compositions may also be formulated in rectal compositions, such as suppositories (e.g., with conventional suppository bases such as cocoa butter and other glycerides) or retention enemas.

Pharmaceutical compositions suitable for injectable use include sterile aqueous solutions (where water soluble) or dispersions and sterile powders for the extemporaneous preparation of sterile injectable solutions or dispersion. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. For example, depending on the injection site, the vehicle may contain water, synthetic or vegetable oil, and/or organic co-solvents. In certain instances, such as with lyophilized product or a concentrate, the parenteral formulation would be reconstituted or diluted prior to administration. pH can be adjusted with acids or bases, such as hydrochloric acid or sodium hydroxide. Depot formulations, providing controlled or sustained release of an invention composition, may include injectable suspensions of nano/micro particles or nano/micro or non-micronized crystals.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, poly(ol) (for example, glycerol, propylene glycol, and liquid polytheylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating the composition in the required amount in an appropriate solvent with one or a com-bination of ingredients enumerated above, as required, followed by filtered sterilization. Prevention of the action of microorganisms can be achieved by various antibacterial and antifungal agents, for example, parabens, chlorobutanol, phenol, ascorbic acid, thimerosal, and the like.

Generally, dispersions are prepared by incorporating the active composition into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin. The parenteral preparation can be enclosed in ampoules, disposable syringes or multiple dose vials made of glass or plastic.

For acupunctural injection or for herbal drug acupuncture or pharmacopuncture, the compositions may be formulated in a needle form. For example, in embodiments, the compositions as described herein cover or coat the acupuncture needle, e.g., made of stainless steel or copper.

Examples of pharmaceutically or physiologically or nutraceutically acceptable carriers, diluents or excipients include, but are not limited to, antifoaming agents, antioxidants, binders, carriers or carrier materials, dispersing agents, viscosity modulating agents, diluents, filling agents, lubricants, glidants, plasticizers, solubilizers, stabilizers, suspending agents, surfactants, viscosity enhancing agents, and wetting agents.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compositions and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compositions disclosed herein and the release profile properties of the desired dosage form. Exemplary carrier materials include, e.g., binders, suspending agents, disintegration agents, filling agents, surfactants, solubilizers, stabilizers, lubricants, wetting agents, diluents, and the like. A "pharmaceutically acceptable carrier," or a "nutraceutically acceptable carrier" as used herein, is intended to include any and all solvents, including water, dispersion media, coatings, antibacterial and antifungal agents, isotonic and absorption delaying agents, anti-inflammatory, stabilizers, and the like, compatible with pharmaceutical or nutraceutical administration. The use of such media and agents for pharmaceutically or nutraceutically active substances is well known in the art. The indication to be treated, along with the physical, chemical, and biological properties of the drug, dictate the type of formulation and the route of administration to be used, as well as whether local or systemic delivery would be preferred. Except insofar as any conventional media or agent is incompatible with the active agent, use thereof in the compositions is contemplated.

Supplementary active agents can also be incorporated into the compositions. Carrier molecules may be genes, polypeptides, antibodies, liposomes or indeed any other agent provided that the carrier does not itself induce toxicity effects or cause the production of antibodies that are harmful to the individual receiving the pharmaceutical composition. Further examples of known carriers include polysaccharides, polylactic acids, polyglycolic acids and inactive virus particles.

Carriers may also include pharmaceutically or nutraceutically acceptable salts such as mineral acid salts (for example, hydrochlorides, hydrobromides, phosphates, sulphates) or the salts of organic acids (for example, acetates, propionates, malonates, benzoates). Pharmaceutically or nutraceutically acceptable carriers may additionally contain liquids such as water, saline, glycerol, ethanol or auxiliary substances such as wetting or emulsifying agents, pH buffering substances and the like. Carriers may enable the pharmaceutical or nutraceutical compositions to be formulated into tablets, pills, dragees, capsules, liquids, gels, syrups, slurries, suspensions to aid intake by the patient.

"Pharmaceutically compatible carrier materials" or "nutraceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. Various formulations and drug delivery systems are available in the art, and a thorough discussion of pharmaceutically acceptable carriers are available in the art. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Also, the separate components of the compositions of the invention may be preblended or each component may be added separately to the same environment according to a predetermined dosage for the purpose of achieving the desired concentration level of the treatment components and so long as the components eventually come into intimate admixture with each other. Further, the invention may be administered or delivered on a continuous or intermittent basis.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the compositions and the particular therapeutic effect to be achieved, and the limitations inherent in the art of compounding such an agent for the treatment of subjects.

In embodiments, a pharmaceutical or a nutraceutical formulation comprises a composition comprising an herbal extract mixture prepared by mixing a combination of herbs and obtaining the herbal extract from the combination of herbs. In embodiments, a pharmaceutical or a nutraceutical formulation comprises a composition comprising an herbal extract mixture prepared by mixing a combination of herbal extracts prepared from each herb. In embodiments, the composition comprising an herbal extract mixture prepared by mixing a combination of herbs and obtaining the herbal extract from the combination of herbs is formulated in a form of a powder, a granule, a tablet, a pill, a capsule, a dragee, a solution, a suspension, an acupunctural needle, a gel, a syrup, a slurry, a suspension, or an emulsion. In embodiments, the herbal extract prepared from each herb is formulated into a pharmaceutical or a nutraceutical formulation, e.g., a powder, a granule, a gel, a syrup, a slurry, a suspension, and an emulsion, and then, a combination of the pharmaceutical or nutraceutical formulations comprising the herbal extract prepared from each herb is mixed and further formulated in a final pharmaceutical or nutraceutical formulation, e.g., in a form of a powder, a granule, a tablet, a pill, a capsule, a dragee, a solution, a suspension, an acupunctural needle, a gel, a syrup, a slurry, a suspension, or an emulsion. In embodiments, a pharmaceutical or nutraceutical formulation comprises a composition comprising the herbal extracts that are further processed, for example, filtered and/or concentrated.

Kits and Compositions

One aspect of the disclosure relates to kits including the compositions for treating diseases or disorders associated with or characterized by neuro-inflammation, neuro-apoptosis, or neuro-oxidative damage. The kits can further include one or more additional therapeutic regimens or agents for treating diseases or disorders associated with or characterized by neuro-inflammation, neuro-apoptosis, or neuro-oxidative damage.

Also disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include the composition of the invention, and optionally in addition with therapeutic regimens or agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1. H1 and H2 ameliorates 1-methyl-4-phenyl-1,2,3,6-tetrahydropyridine hydrochloride (MPTP)-induced decreased neuronal cell viability 1-Methyl-4-phenylpyridinium (MPP+) induces a severe parkinsonian-like syndrome and a significant reduction in dopaminergic cells by the selective inhibition of complex I in the mitochondrial electron transport chain. SH-SY5Y neuronal cells were first treated with various concentrations of MPTP (0, 0.5, 1, 2, 4, and 5 mM) for 24 h, and cell viability was measured by the 3-(4,5-dimethylthiazol-2-yl)-2,5-diphenyltetrazolium bromide (MTT) assay to determine an appropriate concentration for the subsequent study. Cell viability dramatically decreased after treatment with 0.5 mM to 5 mM MPTP (FIG. 1A), and 1 and 2 mM MPTP, causing significant cell death (29.05% and 68.89%, respectively), were selected to investigate the protective effect of Hepad 1 (H1) and Hepad 2 (H2) in subsequent experiments.

Figure 1B:
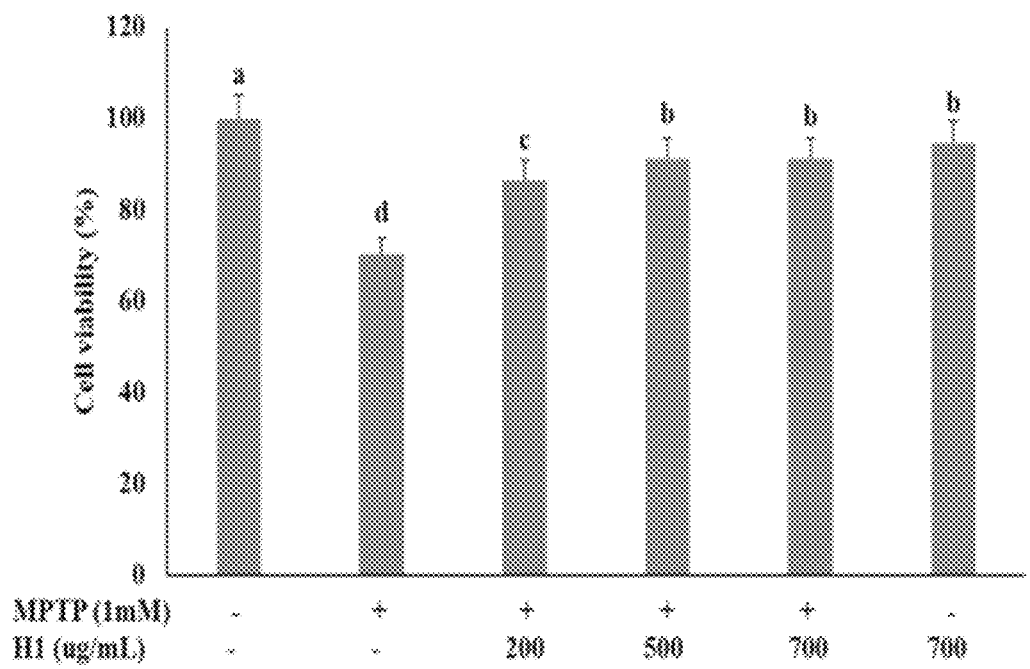
Figure 1B:
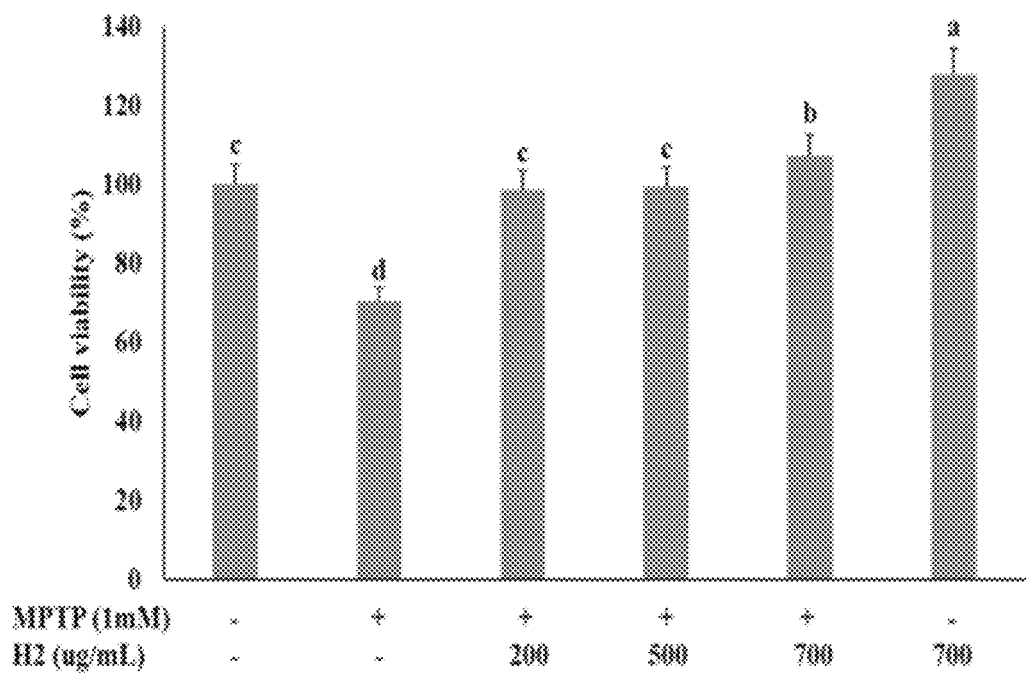
Figure 1C:
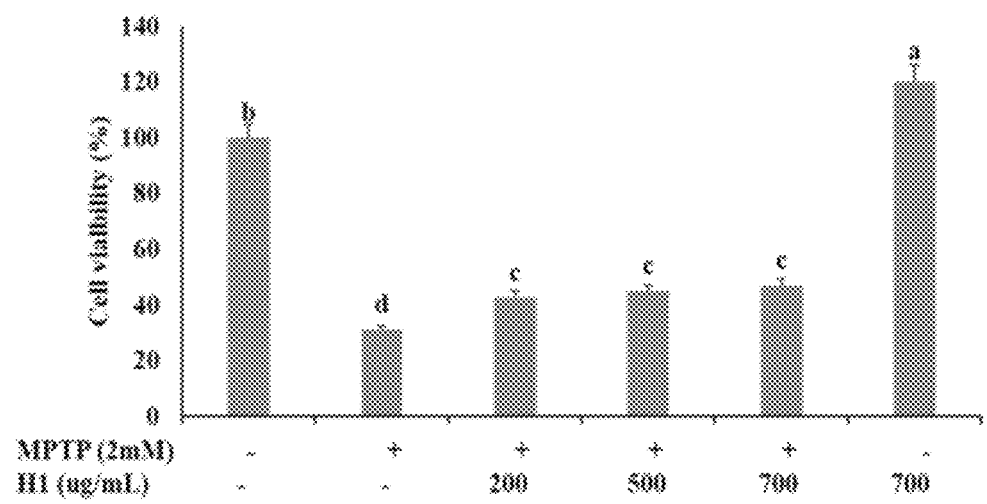
Figure 1C:
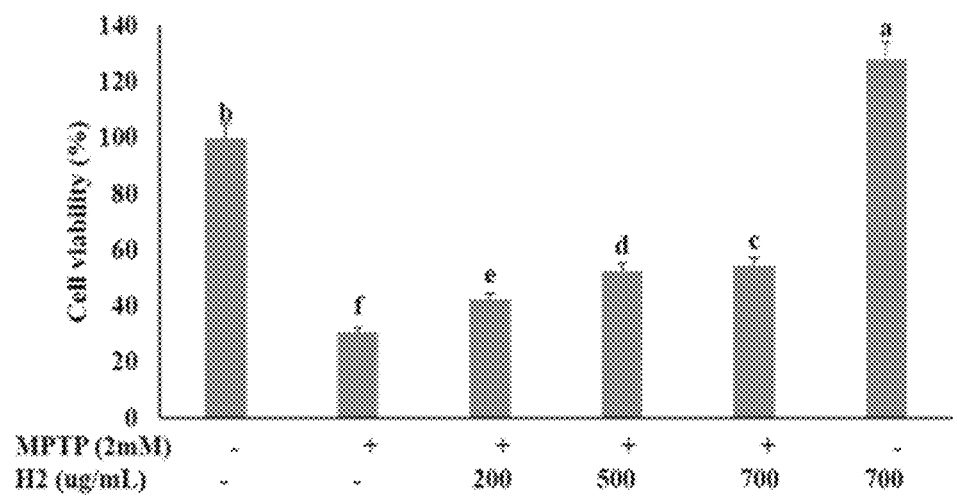

As shown in FIG. 1B, cell viabilities increased by 86.5%, 91.2%, and 91.2% after 200, 500, and 700 µg/mL H1 treatment, respectively, compared with those of MPTP-intoxicated cells. H2 treatment (200, 500, and 700 µg/mL) also alleviated cell toxicity of MPTP in a dose-dependent manner. Especially, 700 µg/mL H2 significantly attenuated (57.6%) the cell toxicity of MPTP (FIG. 1B). In 2-mM MPTP-intoxicated cells, 200, 500, and 700 µg/mL H1 treatment significantly increased cell viability by 42.85%, 44.96%, and 48.97%, respectively (FIG. 1C). Moreover, H2 treatment rescued the reduced cell viability in 2-mM MPTP-treated cells in a concentration-dependent manner, and the cells treated with 700 µg/mL H2 showed the highest viability (48.97%) (FIG. 1C). Therefore, the results demonstrate that H1 and H2 have mitigation effects against impaired neuronal cell viability. Based on these above results, 2 mM MPTP was used in subsequent experiments to examine the mechanism of PD.

Example 2. H1 and H2 Attenuates MPTP-Induced Inflammation

Figure 2A:
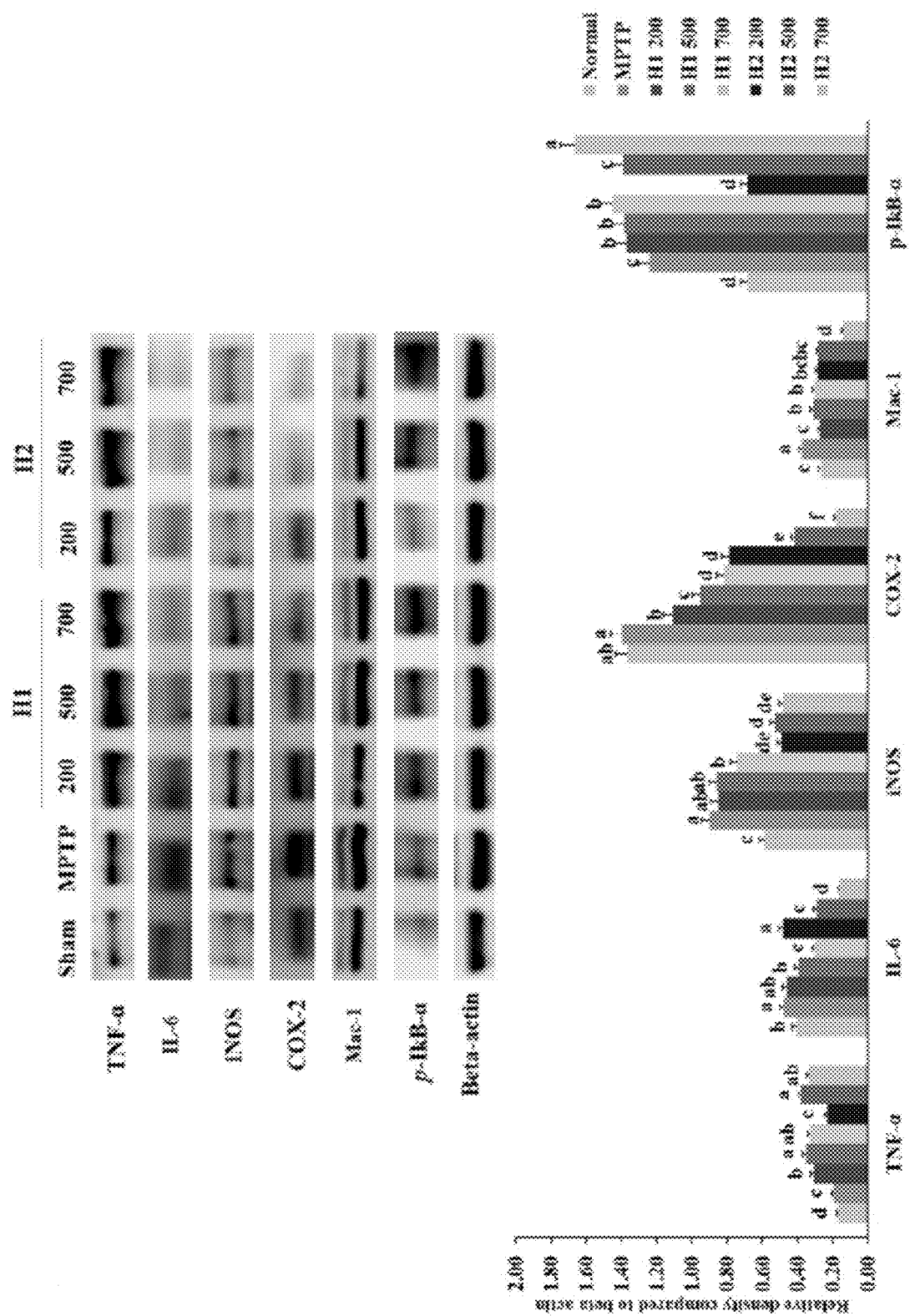
FIGS. 2A and 2B shows alleviation effects of H1 and H2 on increased expression of inflammation-related proteins (FIG. 2A) and apoptosis-related proteins (FIG. 2B) in MPTP-treated SH-SY5Y cells. Results are expressed mean±SD. Values not sharing a common superscript (a, b, c, d, and e) differed significantly (Duncan's multiple range test) ($p<0.05$).

To investigate the anti-inflammatory effect of H1 and H2, whether H1 and H2 affect the activation of TNF-α, IL-6, inducible nitric oxide synthase (iNos), COX-2, macrophage-1 (Mac-1), and phosphorylated ikappaB-alpha (p-IκB-α) was examined. As shown in FIG. 2A, a slight increase in TNF-α protein expression levels was found in MPTP-intoxicated cells compared with normal cells, and the increase was attenuated by 200, 500, and 700 µg/mL H1 treatments. In addition, H2 treatment (200, 500, and 700 µg/mL) alleviated the increased expression of TNF-α in a concentration-dependent manner (FIG. 2A).

The level of IL-6 increased in MPTP-treated cells but was significantly reduced to the normal level after treatment with 200, 500, and 700 µg/mL of H1 (FIG. 2A). Moreover, H2 treatment dose-dependently decreased the expression levels of IL-6 (FIG. 2A). Therefore, H1 and H2 treatment suppresses IL-6 expression, which is associated with activated inflammatory cytokines. The results indicate anti-inflammatory effects of H1 and H2 in the MPTP-intoxicated cells. Moreover, MPTP stimulated the secretion of iNOS, but the secretion was blocked by H1 and H2 treatment (FIG. 2A).

MPTP induced the secretion of COX-2 in SH-SY5Y cells, and the increased secretion was repressed by treatment with 200, 500, and 700 µg/mL of H1 (1.3-, 1.5-, and 1.7-folds, respectively) (FIG. 2A). Furthermore, the protein expression level of Cox-2 significantly decreased by 1.8-, 3.4-, and 7.7-folds in MPTP-intoxicated cells after treatment with 200, 500, and 700 µg/mL H2, respectively (FIG. 2A).

The protein expression level of Mac-1 was markedly elevated by 0.8-folds in 2-mM MPTP-intoxicated cells compared with normal cells; however, the elevation was attenuated by 200, 500, and 700 µg/mL of H1 (0.8-fold) and H2 (0.8-, 0.8-, and 0.4-folds, respectively) treatment (FIG. 2A).

The protein expression level of p-IκB-α was higher in the MPTP-treated cells (FIG. 2A) than in control cells. MPTP-induced downregulation of p-IκB-α was reversed by H1 and H2 treatment, and 700 µg/mL of H1 or H2 exhibited maximum effects (FIG. 2A). Therefore, western blotting analysis demonstrates that inflammation response proteins play a pivotal role in MPTP-induced inflammation. These results also indicate that the expression levels of inflammation-related proteins, such as IL-6, COX-2, and Mac-1, decrease after H1 and H2 treatment. Thus, these results indicate that H1 and H2 has a mitigating effect on PD-associated pathology.

Figure 2B:
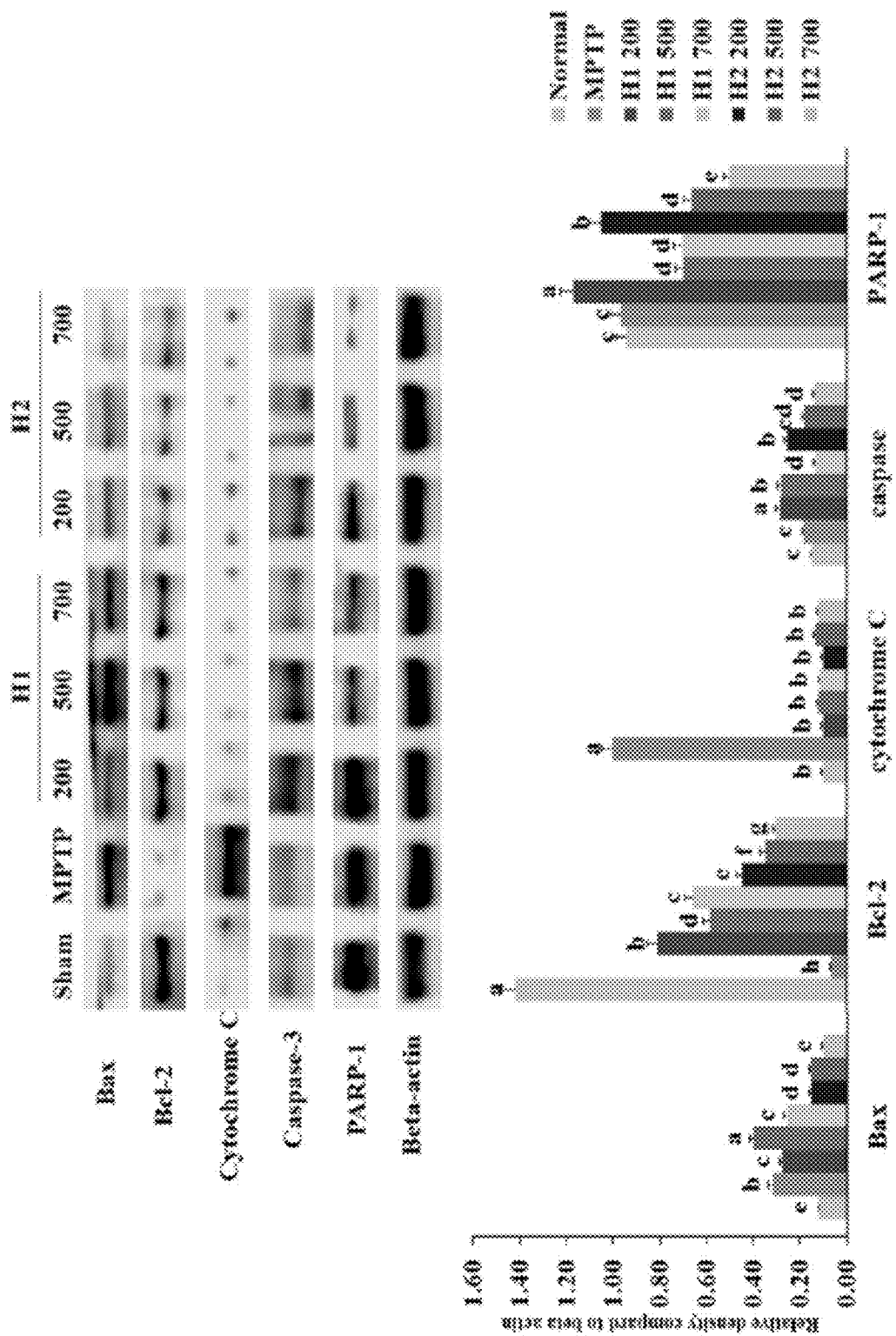

Example 3. Effects of H1 and H2 on Proapoptosis and Antiapoptosis Protein Expression in MPTP-Intoxicated SH-SY5Y Cells To evaluate the anti-apoptotic signal mechanism after H1 and H2 treatment, whether H1 and H2 alters the activation of proapoptotic and antiapoptotic proteins was investigated. As shown in FIG. 2B, levels of Bax robustly increased after treatment with MPTP, but H1 and H2 suppressed the increased expression of Bax in SH-SY5Y cells. In contrast, the expression of anti-apoptotic protein Bcl-2 was inhibited in the MPTP-treated cells but was elevated in cells treated with 200, 500, and 700 µg/mL of H1 and H2 (FIG. 2B).

The protein expression level of cytochrome C was dramatically upregulated (10-folds) in MPTP-intoxicated cells. However, 200, 500, and 700 µg/mL H1 and H2 treatment markedly inhibited the upregulation, and the protein expression level of cytochrome C after H1 and H2 treatment was comparable with that in normal control cells (FIG. 2B).

MPTP induced cleavage of caspase 3, but this cleavage was inhibited by 700 µg/mL of H1 and H2 treatment. The protein expression levels of poly (ADP-ribose) polymerase-1 (PARP-1) were lower in cells treated with 200, 500, and 700 µg/mL H1 than in MPTP-treated cells (FIG. 2B). In addition, treatment with H2 (200, 500, and 700 µg/mL) decreased the protein expression levels of PARP-1 in a dose-dependent manner (by 1.09-, 0.69-, and 0.52-folds, respectively) (FIG. 2B). Therefore, H1 and H2 is proposed to be an alleviation agent for PD through suppressing the activation of the apoptosis signaling pathway.

Example 4. H1 and H2 Suppresses MPTP-Induced Oxidative Stress

Figure 3A:
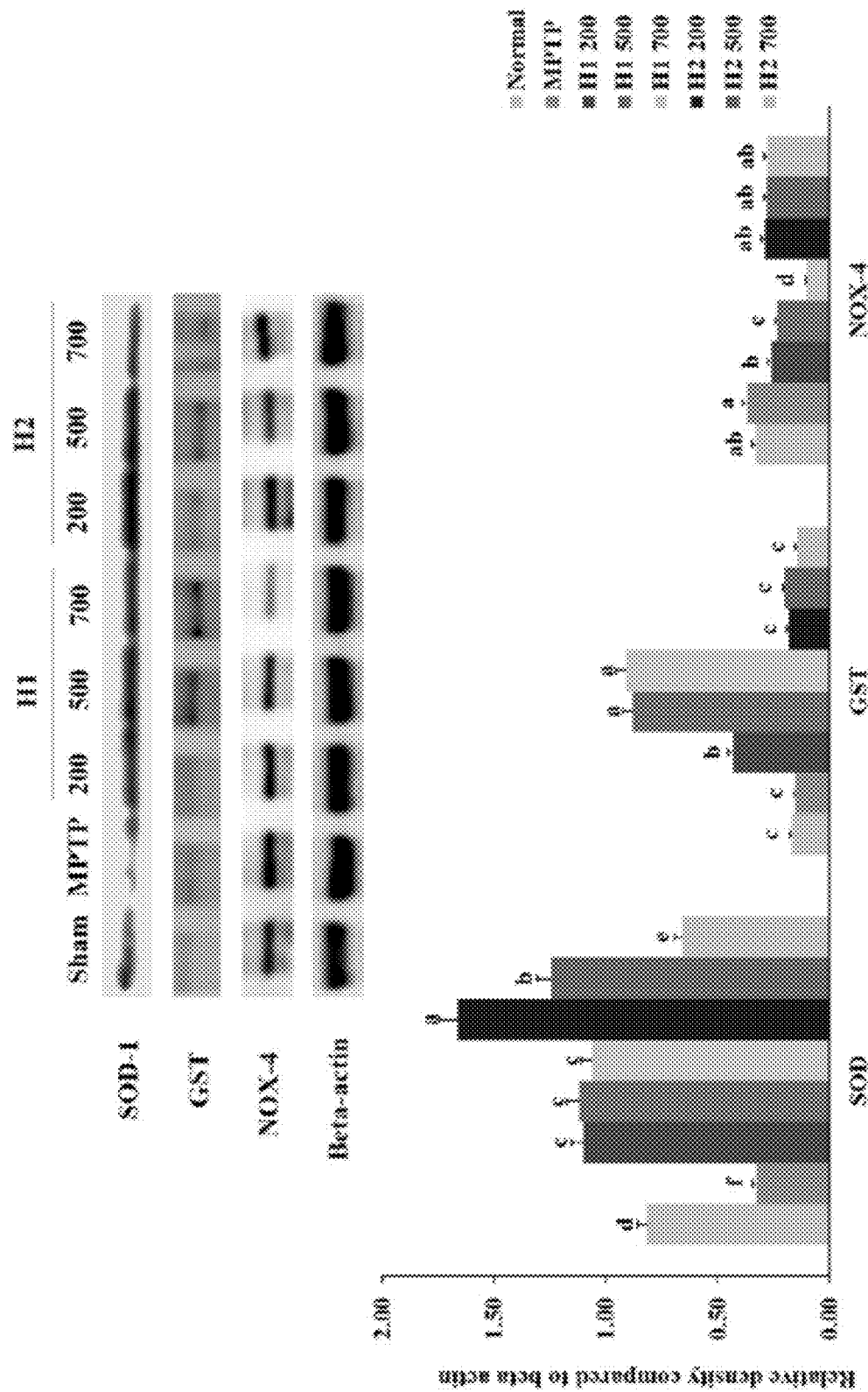
FIGS. 3A and 3B shows mitigation effects of H1 and H2 on the expression of antioxidant enzymes in MPTP-treated SH-SY5Y cells (FIG. 3A). Protein expression levels of protein kinase B (AKT), c-Jun N-terminal kinase (JNK), and extracellular and signal-regulated kinase (ERK) in MPTP-treated SH-SY5Y cells (FIG. 3B). Results are expressed as mean±SD. Values not sharing a common superscript (a, b, c, d, and e) differed significantly (Duncan's multiple range test) ($p<0.05$).

The protein expression level of superoxide dismutase (SOD) decreased in MPTP-intoxicated cells compared with normal cells. In contrast, the expression level of SOD was higher in H1-treated cells than in MPTP-intoxicated cells, but no significant differences were found among different concentrations of H1 treatment (FIG. 3A). Notably, H2 treatment increased protein expression levels of SOD in a concentration-dependent manner (FIG. 3A). Similarly, the expression level of glutathione S-transferase (GST) was slightly downregulated in MPTP-intoxicated cells; exposure to MPTP resulted in increased activation of nicotinamide adenine dinucleotide phosphate oxidase 4 (NOX-4), but the activation was significantly inhibited by treatment with 200, 500, and 700 µg/mL H1 (0.7-, 0.63-, and 0.27-folds, respectively). Similarly, H2 treatment also decreased the expression levels of Nox-4, but the differences were not statistically significant (FIG. 3A).

Figure 3B:
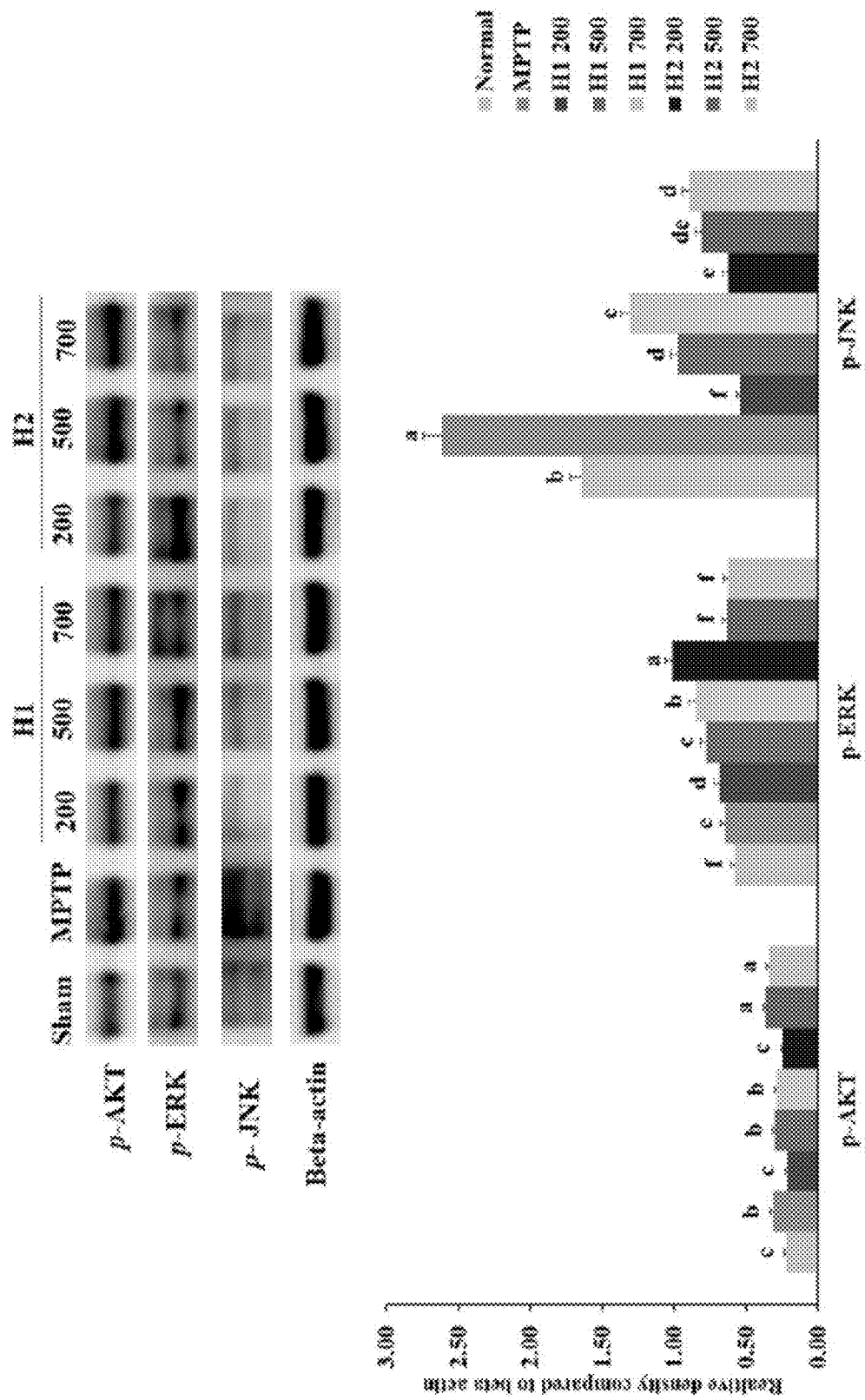

Example 5. H1 and H2 Attenuates the Elevation of Phosphorylated Protein Kinase B (p-AKT) and Mitogen-Activated Protein Kinase (MAPK) in MPTP-Intoxicated SH-SYSY Cells The effect of H1 and H2 on p-AKT, phosphorylated extracellular-signal-regulated kinase (p-ERK), and phosphorylated c-Jun N-terminal kinase (p-JNK) was assessed in MPTP-stimulated SH-SYSY cells. Treatment with 200, 500, and 700 µg/mL H1 or H2 markedly suppressed the increase in p-AKT in MPTP-intoxicated cells in a dose-dependent manner (FIG. 3B).

Stimulation with MPTP increased the level of p-ERK. However, post-treatment with 200, 500, and 700 µg/mL H1 or H2 markedly inhibited the activation of p-ERK in MPTP-intoxicated cells, and the levels of p-ERK decreased by 1.1-, 1.2-, and 1.3-fold after H1 treatment and 1.6-, 1.0-, and 1.0-fold after H2 treatment, respectively (FIG. 3B).

The p-JNK signaling pathway has been implicated in apoptosis mediated by numerous kinds of stress, such as nerve growth factor withdrawal, excitotoxic stress, and oxidative stress. Interestingly, compared with normal cells, MPTP-intoxicated cells showed upregulated protein levels of p-JNK, indicating activated p-JNK in MPTP-intoxicated SH-SYSY cells. Notably, post-treatment of H1 or H2 (200, 500, and 700 μg/mL) attenuated MPTP-induced elevation of p-JNK in SH-SYSY cells (FIG. 3B).

Figure 4A:
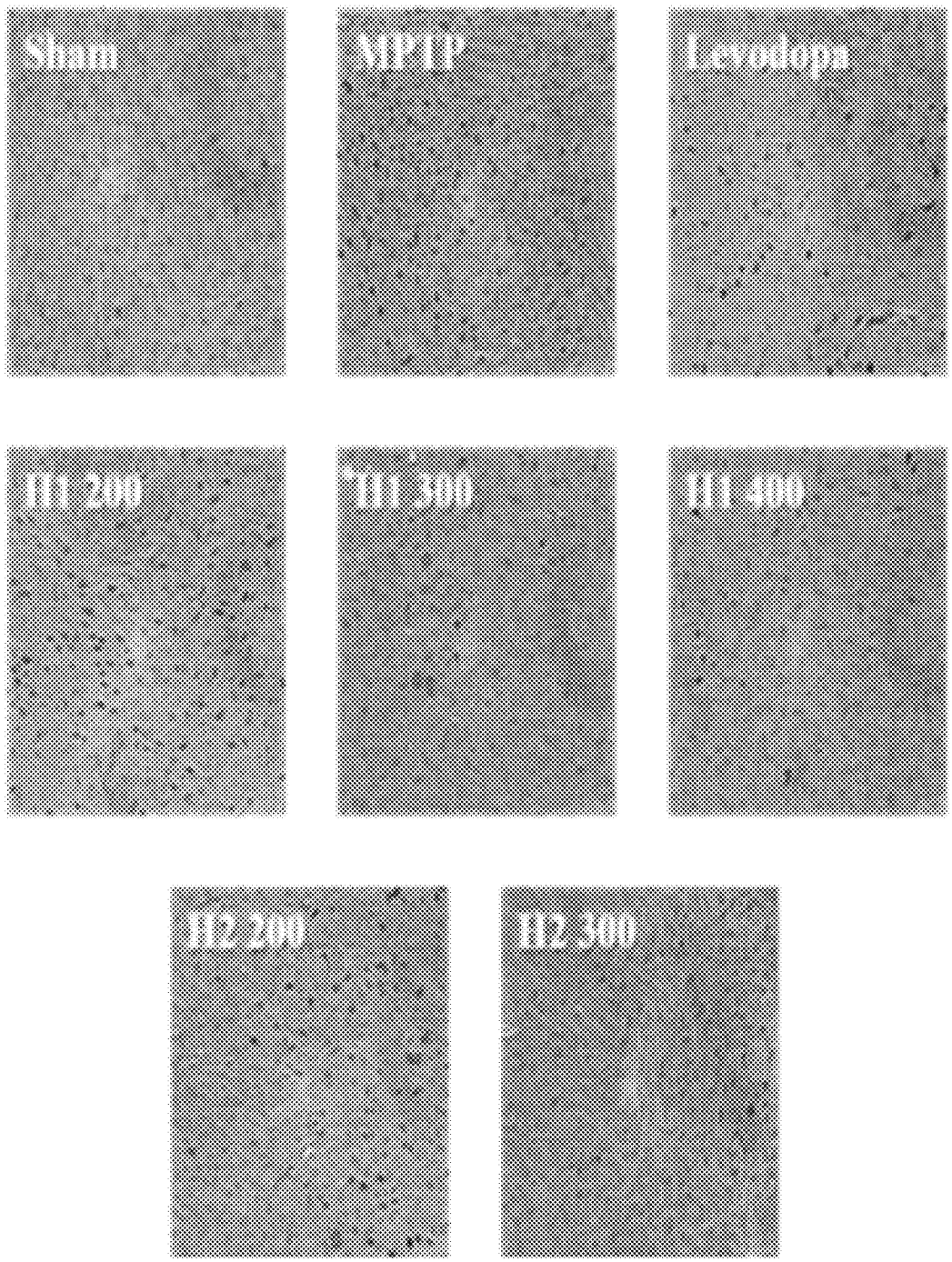
FIGS. 4A and 4B shows exemplary photomicrographs (40× magnification) of hematoxylin and eosin-stained brain sections (FIG. 4A) and immunohistochemical staining of tyrosine hydroxylase (TH) neurons (FIG. 4B) (scale bar, 100 gm). Results (the number of TH+ cells) are expressed as mean±SD (FIG. 4C). Values not sharing a common superscript (a, b, c, d, and e) differed significantly (Duncan's multiple range test) ($p<0.05$).
Figure 4B:
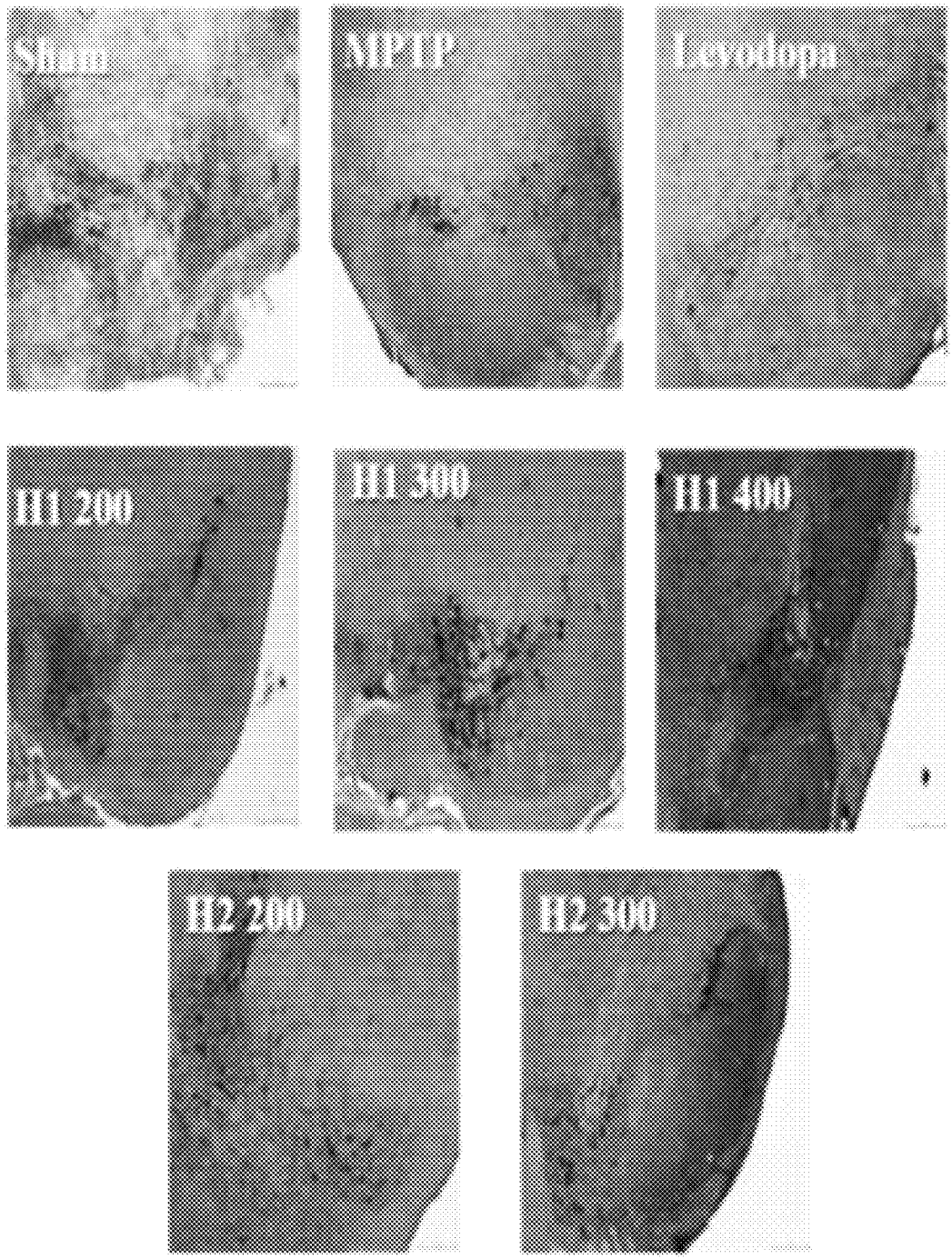

Example 6. Hematoxylin and Eosin (H&E) Staining and Immunohistochemical Detection of Tyrosine Hydroxylase (TH) in the Substantia Nigra Lewy body was observed as a spherical body with a dense core surrounded by a halo in the MPTP-intoxicated mice compared with the sham mice (FIGS. 4A and 4B). MPTP-intoxicated mice showed dopaminergic neuronal damage with loss of multipolar shape and distorted nuclei (FIGS. 4A and 4B). Notably, multipolar neurons with nucleoli and basophilic granular cytoplasm were observed in the SNpc in H1 and H2-treated mice, and the neuronal damage was improved after H1 and H2 treatment in a dose-dependent manner (FIGS. 4A and 4B). The results further demonstrated that H1 and H2 had a better mitigation effect than the positive control, Levodopa.

Figure 4C:
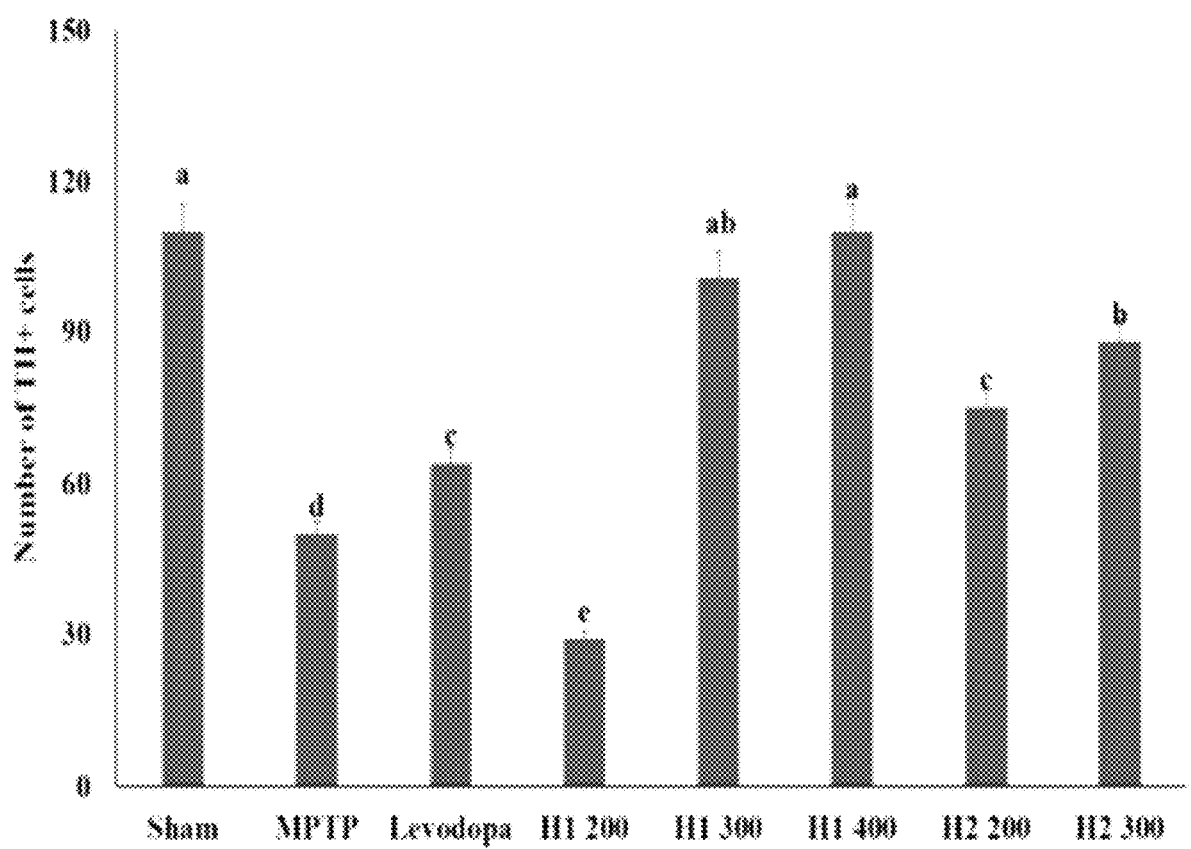

The number of TH-positive cells in the MPTP-intoxicated group was reduced by more than two-fold compared with that in the sham group (FIG. 4C). Numbers of TH-positive cells were significantly elevated in the groups treated with Levodopa, H1 (200, 300, and 400 mg/kg), or H2 (200 and 300 mg/kg) compared with the MPTP-intoxicated group (0.58-folds, 2.0-folds, and 2.2-folds after H1 treatment and 1.5- and 1.76 folds after H2 treatment, respectively) (FIG. 4C).

Example 7. Mitigation Effects of H1 and H2 on MPTP-Induced Inflammatory Responses Inflammatory responses are generally triggered in the MPTP model. The expression of TNF-α was remarkably higher in the MPTP-treated group than in the vehicle-treated group. However, protein expression levels of TNF-α were downregulated in the groups treated with high dose of H1 and H2 compared with the MPTP-treated group (1.0-folds after H1 treatment and 0.7-folds after H2 treatment, respectively) (FIG. 5A).

Figure 5A:
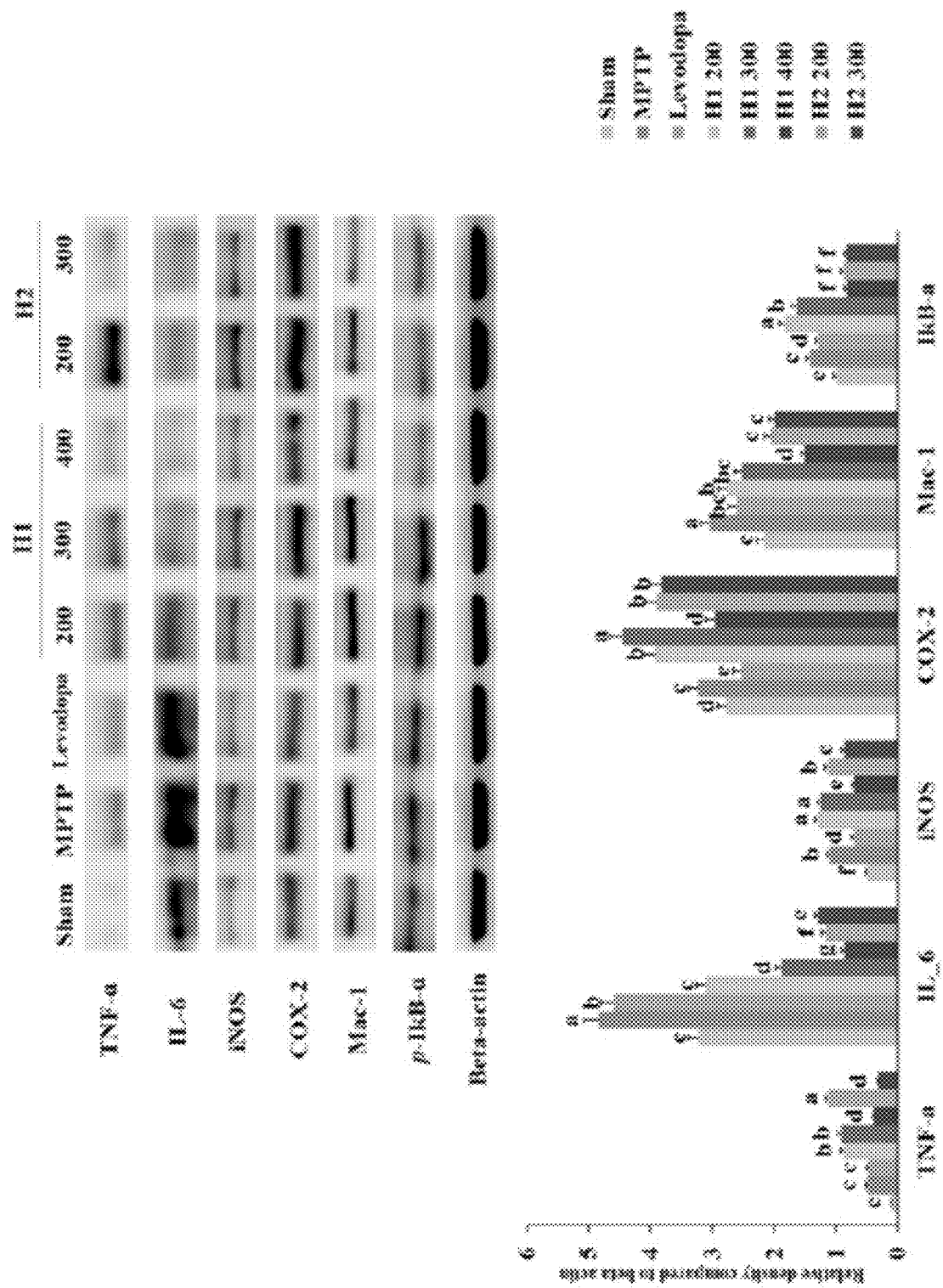

Additionally, the IL-6 protein expression level significantly increased in MPTP-treated mice, but the increase of the protein levels of IL-6, which is an inflammation-related protein, was dose-dependently attenuated by 6.4-, 3.9-, and 1.8-folds after H1 treatment and 2.3- and 0.6-folds after H2 treatment, respectively (FIG. 5A).

The iNos protein expression level was elevated by 0.44-folds in the MPTP-treated group compared with the sham group, but the elevation of expression was inhibited by H1 and H2 treatment (2.6-, 2.6-, and 1.5-folds after H1 treatment and 2.3- and 1.8-folds after H2 treatment, respectively), as did Levodopa treatment (FIG. 5A). Furthermore, MPTP significantly increased COX-2 activity, and 200 μg/mL H1 and H2 attenuated MPTP-induced increase of COX-2 (FIG. 5A).

Mac-1 protein levels were lower in the groups treated with 200, 300, and 400 mg/kg H1 (5.7-, 5.2-, and 3.1-folds, respectively) than in the MPTP-treated group, and the decrease is dose-dependent (FIG. 5A). In addition, Mac-1 expression was reduced in the groups treated with 200 and 300 mg/kg H2 (4.3- and 4.1-fold, respectively) compared with the MPTP-intoxicated group (FIG. 5A).

p-IκB-α levels were significantly elevated after MPTP injection, and Levodopa slightly restored the increased p-IκB-α level (FIG. 5A). In addition, p-IκB-α levels were downregulated in the groups treated with 200, 300 and 400 mg/kg H1 compared with the MPTP-intoxicated group, and the downregulation is concentration-dependent. Moreover, 200 and 300 mg/kg H2 also significantly reduced the p-IκB-α protein expression level (FIG. 5A). Together, H1 and H2 downregulated MPTP-induced increase in all inflammation-related proteins, such as TNF-α, IL-6, iNos, Mac-1, and p-IκB-α (FIG. 5A). Therefore, these results demonstrate the mitigation effect of H1 and H2 on neuroinflammation in the MPTP-induced mouse model of PD.

Figure 5B:
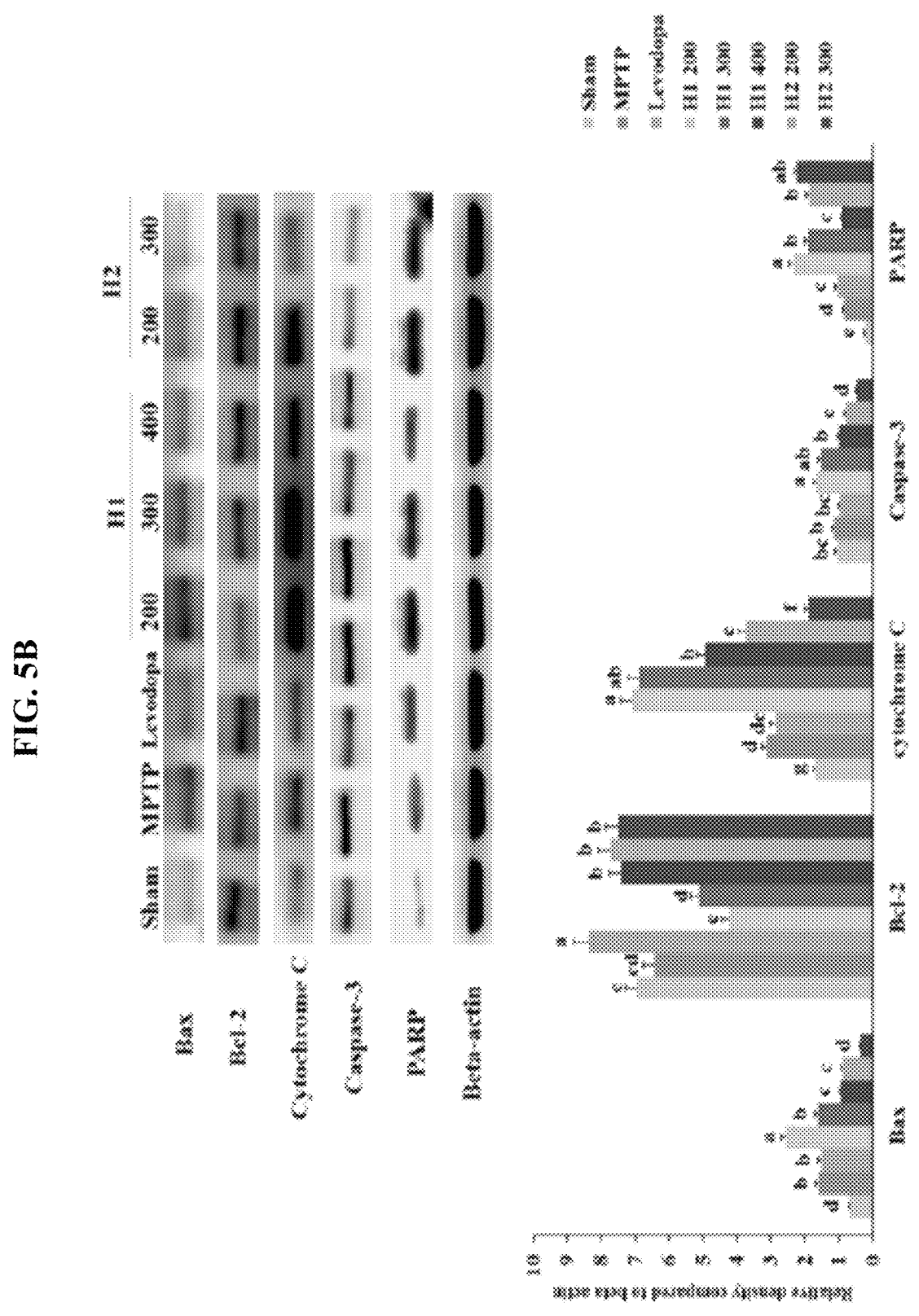

Example 8. H1 and H2 Affects the Activation of Proapoptosis and Antiapoptosis Proteins To examine the effect of H1 and H2 on MPTP-induced cell apoptosis, several proteins involved in the apoptotic process were investigated. MPTP treatment increased Bax protein expression levels, which could be reduced by 400 mg/kg H1 (0.6-fold) and 200 and 300 mg/kg H2 (0.6- and 0.2-folds, respectively) treatment (FIG. 5B). In addition, the effects of MPTP on Bcl-2 protein expression were significantly reversed by 200, 300, and 400 mg/kg H1 (0.7-, 0.8-, and 1.1-folds, respectively) and 200 and 300 mg/kg H2 treatment, as did Levodopa (positive control) (FIG. 5B).

The protein expression level of cytochrome C was apparently upregulated by 0.54-folds in MPTP-intoxicated mice compared with sham mice (FIG. 5B). However, the upregulation was suppressed in mice treated with 200, 300, and 400 mg/kg H1 or 200 and 300 mg/kg H2 (2.3-, 2.2-, and 1.6-folds after H1 treatment and 1.2- and 0.6-folds after H2 treatment, respectively) (FIG. 5B).

The expression levels of cleavage caspase-3 in the H1 (200, 300, and 400 mg/kg) and H2 (200 and 300 mg/kg)-treated groups significantly decreased in a dose-dependent manner, as compared with those in the MPTP-treated group ($p<0.05$) (FIG. 5B). Remarkably, the protein expression of PARP-1 was higher in the MPTP-treated group than in the sham group. H1 treatment (200, 300, and 400 mg/kg) robustly blocked MPTP-induced upregulation of PARP-1 (2.8-, 2.2-, and 1.1-folds, respectively) (FIG. 5B). In addition, treatment with H2 (200 and 300 mg/kg) also inhibited the increase of PARP-1 (FIG. 5B). Therefore, H1 and H2 treatment effectively attenuates proapoptosis signal and increases antiapoptosis signals in the brain exposed to MPTP stimulation.

Example 9. H1 and H2 Inhibits MPTP-Induced Oxidative Stress

The expression level of SOD is statistically lower (2.3-folds) in the MPTP-treated group than in the sham group, and H1 treatment with indicated doses (200, 300, and 400 mg/kg) markedly inhibited MPTP-induced decrease in SOD (0.98-, 0.98-, and 2.19 folds, respectively). In addition, H2 treatment inhibited the decrease of SOD in a concentration-dependent manner (FIG. 6A).

Figure 6A:
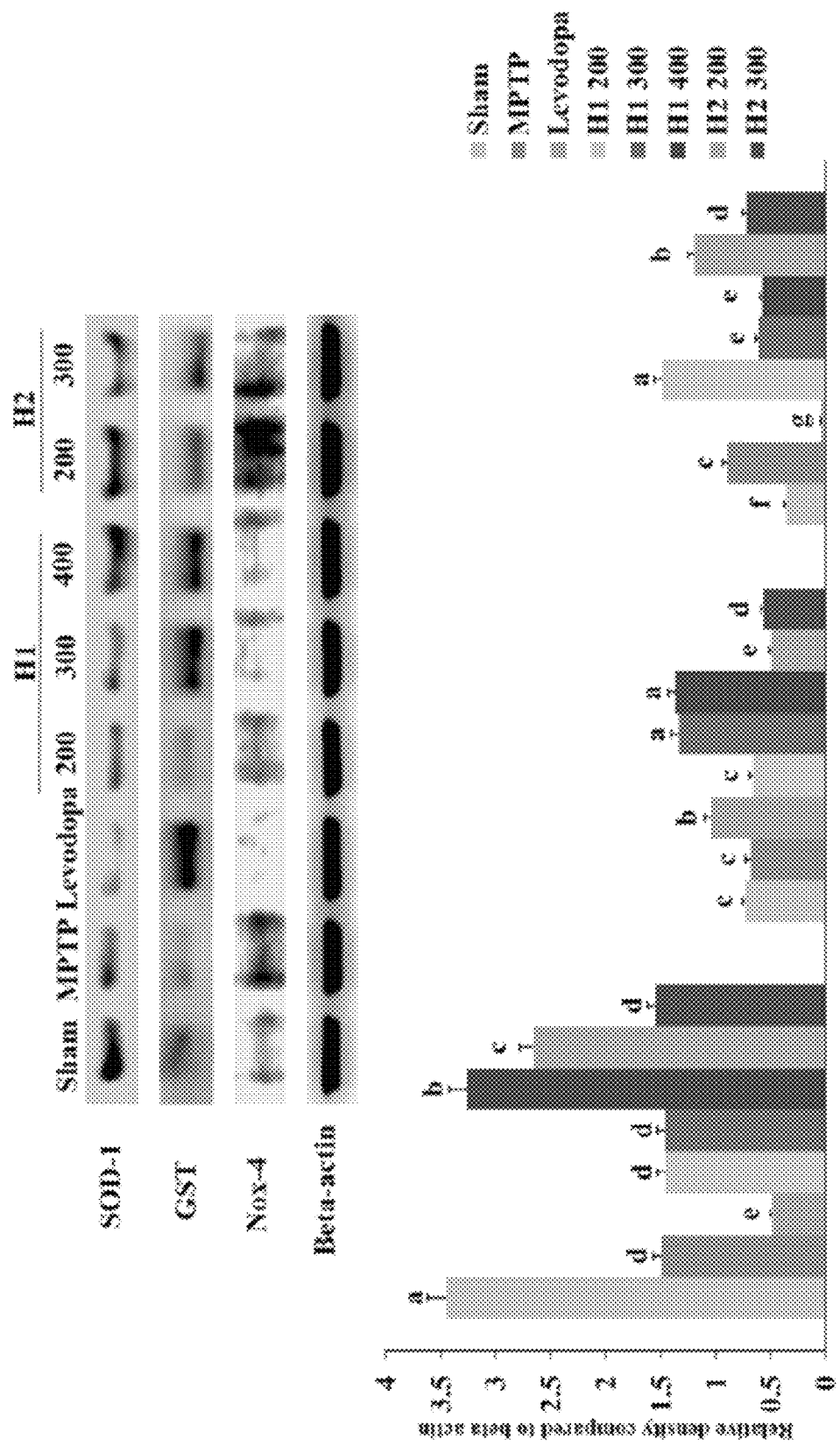
FIG. 6A shows effects of H1 and H2 on the expression of antioxidant-related proteins in the brains in the PD model. Superoxide dismutase (SOD), glutathione-S-Transferase (GST), and nicotinamide adenine dinucleotide phosphate oxidase 4 (Nox-4) levels were assessed by western blotting.

Similarly, MPTP injection increased the GST level, and 200, 300, and 400 mg/kg H1 (1.0, 2.9-, and 2.0-folds, respectively) and 200 and 300 mg/kg H2 (0.7- and 0.8-folds, respectively) inhibited the effect of MPTP stimulation (FIG. 6A). In addition, MPTP injection upregulated the expression of NOX-4, but H1 (200, 300, and 400 mg/kg) and H2 (200 and 300 mg/kg) significantly decreased the expression level of NOX-4 (1.7-, 0.7-, and 0.6-folds after H1 treatment and 1.3- and 0.8-folds after H2 treatment, respectively) (FIG. 6A).

Example 10. H1 and H2 Modulates the p-AKT and MAPK Signal Pathway

Figure 6B:
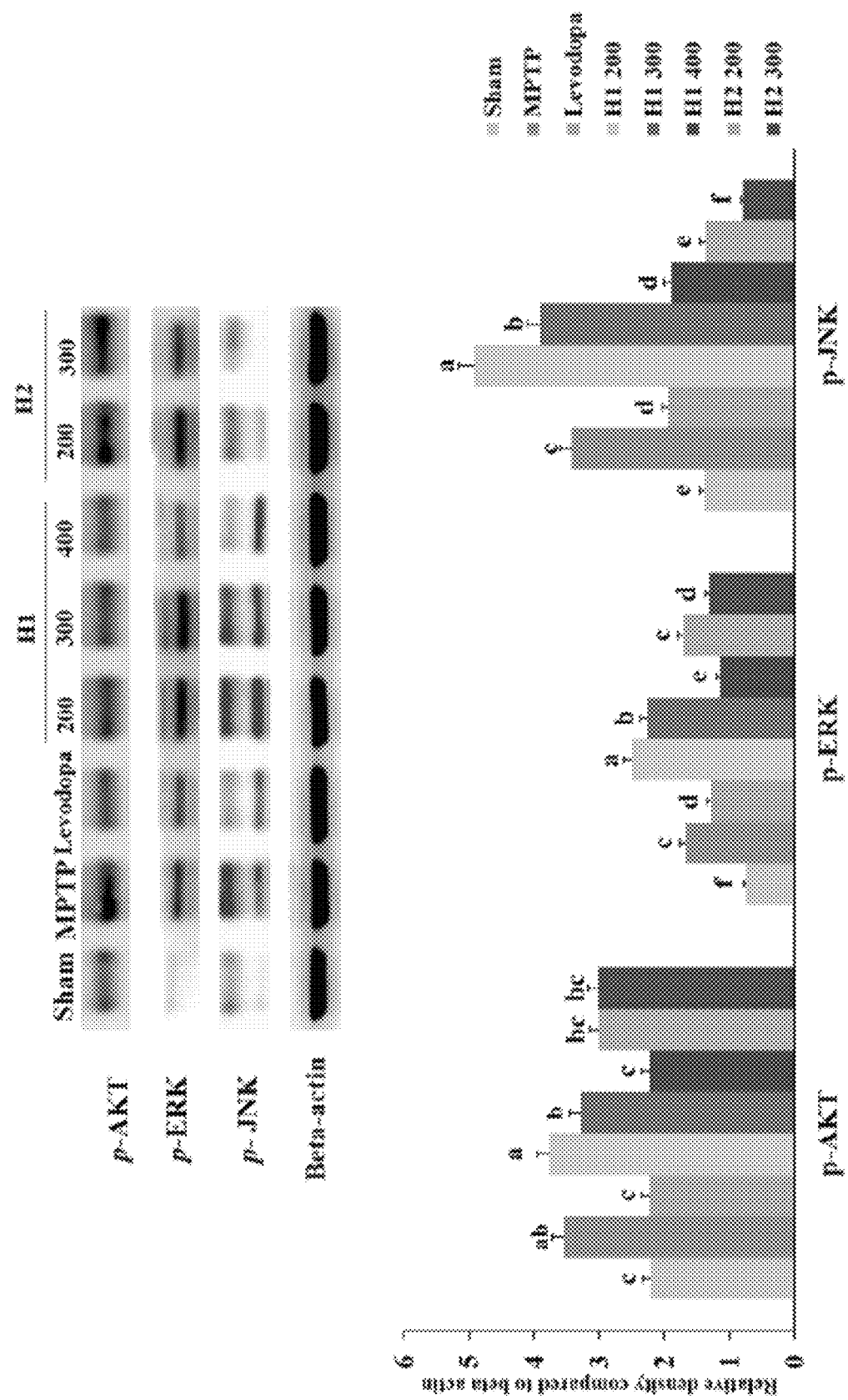
FIG. 6B shows effects of H1 and H2 on the expression of phosphorylated-(p-) AKT, p-ERK, and p-JNK in the brain in the PD model. Results are expressed as mean±SD. Values not sharing a common superscript (a, b, c, d, and e) differed significantly (Duncan's multiple range test) ($p<0.05$).

MPTP stimulation increased the protein expression levels of p-AKT, p-ERK, and p-JNK in the SN, but the alternation was reversed by H1 and H2 treatment (FIG. 6B). MPTP-induced increase in the p-AKT level was attenuated by treatment with 200, 300, and 400 mg/kg H1 (1.1-, 0.9-, and 0.6-folds, respectively) (FIG. 6B). Moreover, the increase in the p-AKT level was slightly inhibited in the groups treated with 200 and 300 mg/kg H2. Expression of p-ERK was increased by MPTP treatment (FIG. 6B), and H1 and H2 attenuated the increase in the protein expression of p-ERK (1.5-, 1.3-, and 0.7-folds after H1 treatment and 1.0- and 0.8-folds after H2 treatment, respectively). Moreover, the upregulation of p-JNK level was also diminished by H1 and H2 treatment (FIG. 6B).

In summary, PD is a common adult-onset neurodegenerative disorder characterized by the degeneration of dopaminergic nigrostriatal neurons with complex pathological mechanisms. The data provided herein demonstrated that H1 and H2 protected against MPTP-induced dopaminergic neurotoxicity in C57BL/6 mice and SH-SY5Y cells. Treatment with H1 and H2 remarkably alleviated the increase of pro-inflammation cytokines (tumor necrosis factor-α, interleukin-6, inducible nitric oxide synthase, cyclooxygenase-2, macrophage-1, and phosphorylated ikappaB-alpha) and apoptotic signals (Bcl-2-associated X protein, cytochrome C, caspase-3, and Poly [ADP-ribose] polymerase-1). In addition, H1 and H2 reduced MPTP-induced oxidative damage via increasing expression of antioxidant defense enzymes (superoxide dismutase and glutathione S-transferase) and downregulating the levels of nicotinamide adenine dinucleotide phosphate oxidase 4. Moreover, neuroprotective effects of H1 and H2 are not only related to anti-inflammatory, anti-apoptotic, and antioxidant properties, but also involve the activation of protein kinase B, extracellular-signal-regulated kinase, and c-Jun N-terminal kinase signal pathways. In addition, oral administration of H1 and H2 attenuated cell death of tyrosine hydroxylase-positive substantia nigra neurons induced by 20 mg/kg MPTP. Therefore, these results indicate that H1 and H2 are useful for the treatment of PD and other disorders associated with or characterized by neuro-inflammation, neuro-apoptosis, and neuro-oxidative damage.

The crucial characteristics of Parkinsonism, including dysfunctional motor function, decreased dopamine contents, and reduced dopaminergic neurons (cell bodies and axonal terminals) in the nigrostriatal system, were replicated in MPTP-intoxicated mice. The data presented herein, for the first time, show that H1 containing *Atractylodis Rhizoma, Cnidii Rhizoma, Paeonia japonica, Poria cocos* Wolf; *Uncariae Ramulus* Et Uncus and *Zizyphi Semen* and H2 containing *Paeonia japonica, Uncariae Ramulus* Et Uncus and *Machilus thunbergii* provide the neuroprotective effects through regulation of inflammation, antioxidant enzymes, and apoptosis in the SH-SY5Y cell and mouse PD models induced by MPTP.

Chronic inflammation is associated with a broad spectrum of aging-associated neurodegenerative diseases, including Alzheimer's disease (AD), PD, amyotrophic lateral sclerosis (ALS), tauopathies, and age-related macular degeneration. Especially, the inflammatory responses, which are characterized by activation of microglia and accumulation of inflammatory mediators (such as inflammatory cytokines and proteases) in the SN and striatum, are thought to be responsible for the progression of PD. As shown herein, treatment with 20 mg/kg MPTP caused PD symptoms in SH-SY5Y cell and mouse PD models, as indicated by significantly increased levels of inflammatory cytokines, such as TNF-α, IL-6, iNOS, COX-2, Mac-1, and IκB-α ($p < 0.05$). Thus, inflammatory responses are upregulated in the PD model. Moreover, the mitigation effect of H1 and H2 on the changes in pro-inflammatory cytokines and mediators were assessed in the SH-SY5Y cell and mouse PD models. Interestingly, MPTP increased the expression levels of TNF-α, IL-6, iNOS, COX-2, Mac-1, and P-IκB-α, but the increase was clearly reduced by H1 and H2 treatment. Decreased levels in iNOS, COX-2, p-IκB-α, and Mac-1 regulate anti-inflammatory responses to potentially toxic agents. Therefore, these results indicate the anti-inflammatory potential of H1 and H2 in PD.

The molecular pathogenesis of PD is believed to be associated with mitochondrial dysfunction, oxidative stress, and activation of the apoptotic cascade. SNpc dopaminergic neurodegeneration associated with complex I deficiency occurs, at least partially, through activation of mitochondrion-dependent apoptotic molecular pathways. Activation of the apoptotic cascade may play a role in MPP+-induced cell death by altering mitochondrial membrane permeability and controlling the release of cytochrome C from mitochondria. Activated Caspase-9 and Caspase-3 by released cytochrome C are involved in MPP+-induced apoptosis. Once activated, caspase-3 will induce nuclear DNA condensation and fragmentation and ultimately, apoptosis. MPTP induced apoptotic cell death through Bax and caspase-3, and the expression level of cytochrome C is upregulated by MPTP treatment. Similarly, PARP has also been reported to be cleaved after MPTP treatment. In fact, the data presented herein also showed that MPTP treatment significantly increased the expression levels of the proapoptosis proteins (Bax, cytochrome C, caspase-3, and PARP) and decreased the expression levels of antiapoptosis signals (Bcl-2). The present data indicates that MPTP-induced damages were reversed by H1 and H2 treatment. Thus, the results presented herein demonstrate that H1 and H2 may mitigate the expression of Bax/Bcl-2 proteins in response to MPTP treatment and regulate the mitochondria-mediated downstream molecular events, including the caspase-3 activation and PARP proteolysis.

The impaired integrity of mitochondrial membranes not only destroys the transmembrane proton gradient and interrupts the synthesis of ATP but also indirectly induces increased ROS and loss of enzyme activity and even triggers apoptosis. Recently, oxidative stress has been recognized as an important pathological process of PD. The neurodegeneration of dopaminergic neurons induced by mitochondrial dysfunction and oxidative stress is one of the important features of PD. Moreover, it is a well-established fact that oxidative stress plays a prominent role in the process of aging and makes the neurons more vulnerable to degeneration and the development of neurodegenerative disorders.

Changes in the activity of antioxidant enzymes were detected after MPTP injection. Notably, the expression level of antioxidant enzymes increased after H1 and H2 treatment. These results propose that H1 and H2 could attenuate MPTP-induced dopaminergic neuronal injury due to the ability of H1 and H2 to directly scavenge ROS.

To explore the signaling pathway involved in the neuroprotective effect of H1 and H2, p-AKT, ERK, and JNK signaling pathways were investigated. The levels of p-AKT, ERK½, and JNK increased significantly in MPTP-induced SHSY5Y cell and mouse PD models. Notably, p-AKT levels markedly increased in the MPTP treated group, but H1 and H2 treatment alleviated the upregulation of p-AKT caused by MPTP. These results indicate that H1 and H2 mitigates dopaminergic neuronal damage induced by MPTP via the AKT, ERK, and JNK signaling pathways.

In conclusion, the data presented herein showed for the first time that H1 and H2 had an antioxidant activity and the neuroprotective effects against MPTP-induced oxidative stress injury. Specifically, the results demonstrated that H1 and H2 protected against MPTP-induced injury by reducing the expression of inflammatory regulators (TNF-α, IL-6, COX-2, Mac-1, and p-IκB-α) and apoptosis-associated proteins (Bax, cytochrome C, caspase-3, and PARP-1) and by increasing the levels of antioxidant enzymes (SOD, GST, and NOX-4) via the p-AKT and MAPK (p-ERK and p-JNK) signaling pathways. Therefore, these findings propose that H1 and H2 is a potential therapeutic supplement for the mitigation and treatment of the MPTP-induced cell and brain injury.

Example 11. Materials and Methods Used in Examples 1-10

Preparation of Sample

H1 contains *Atractylodis Rhizoma, Cnidii Rhizoma, Paeonia japonica, Poria cocos* Wolf, *Uncariae Ramulus* Et Uncus, and *Zizyphi Semen* in a 1 to 1 ratio, and H2 contains *Paeonia japonica, Uncariae Ramulus* Et Uncus, and *Machilus thunbergii* in a 1 to 1 ratio. The herbs were extracted in boiling water for 24 h, and the extracts were then collected and filtered. Subsequently, the filtrate was concentrated under reduced pressure at 50° C.

Cell Culture

Human Neuroblastoma Cells (SH-SY5Y) (Korean Cell Bank, Seoul, Korea) were cultured in Dulbecco's modified Eagle's medium containing 10% fetal bovine serum (Hyclone, Logan, Utah, USA) and 1% penicillin-streptomycin (GIBCO, Grand Island, N.Y., USA) in a humidified incubator with 5% $CO_2$ at 37° C.

Cell Viability

SH-SY5Y ($2\times10^6$) cells were cultured in a 96-well plate, and cell viability was determined using the MTT (Promega, Madison, Wis., USA) assay as described previously. Briefly, the cells were treated with various concentrations (200-700 μg/mL) of MPTP (Sigma Aldrich, St. Louis, Mo., USA), Hepad 1 (H1), and Hepad 2 (H2) for 24 h. The MTT solution was then added, followed by incubation at 37° C. for 4 h. The supernatant was removed, and the formed formazan crystals were dissolved in dimethyl sulfoxide. The absorbance of the resulting solution was measured at 540 nm using a UVM 340 microplate reader (Biochrom Asys, Cambridge, UK).

Animal Experiment

Figure 7:
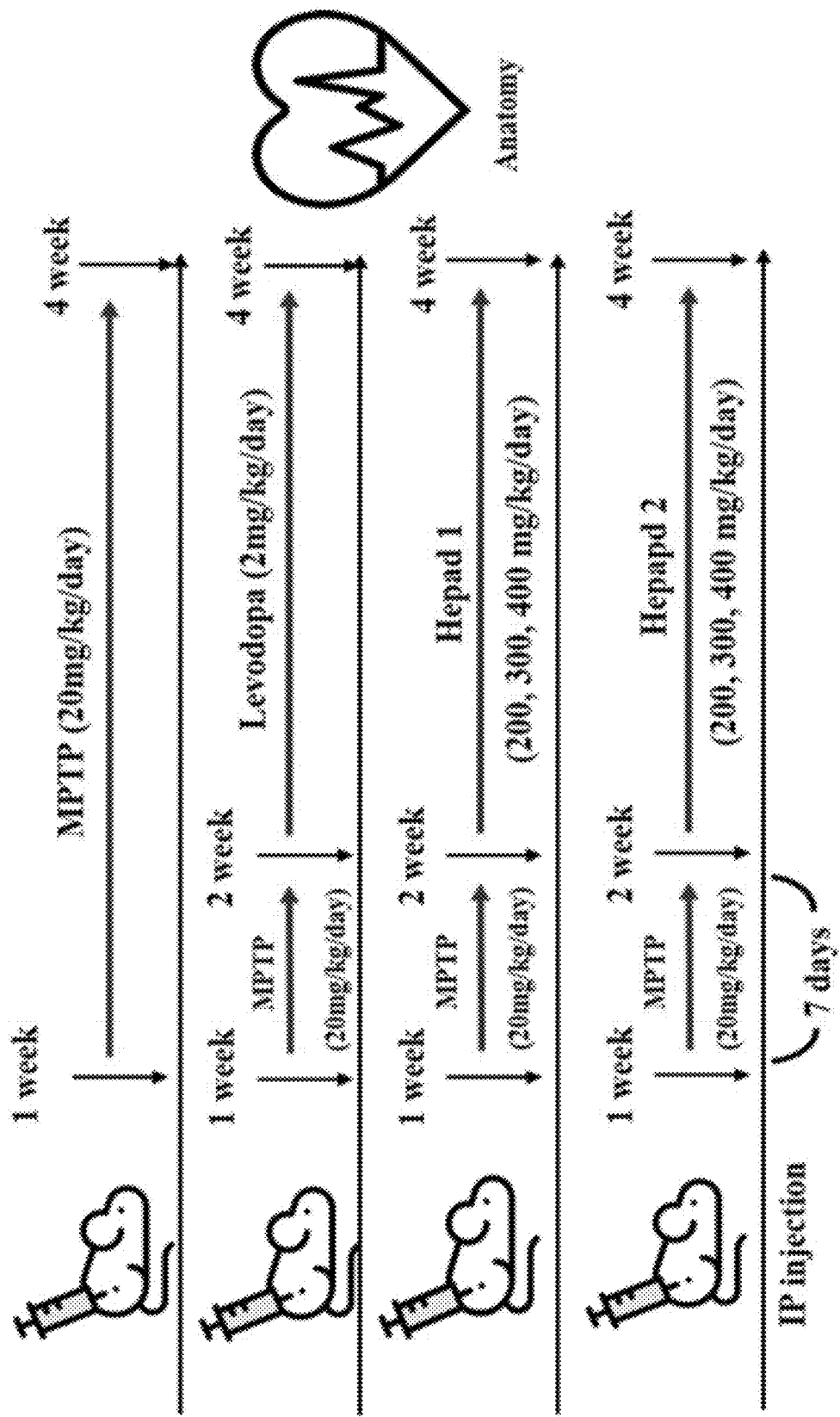
FIG. 7 shows an exemplary flowchart outlining the timeline of the experimental procedures, as described in Examples 1-10.

All experimental animals were approved by the Institutional Animal Care and Use Committee at Konkuk University (IACUC approval number, KU18045), Seoul, Republic of Korea. Seven-week-old male C57BL/6 mice were purchased from Orient Bio, Inc. (Seongnam-si, Korea) and were housed in a temperature-controlled (21-22° C.) and light-controlled (12 h light/dark cycle) environment with 70% humidity, with free access to water and rodent chow. After a one-week period of adaptation, the mice were randomly divided into nine groups (n=8) for MPTP, Hepad 1, and Hepad 2 studies: (l) normal (sham) group, (2) MPTP-treated group, (3) positive group (MPTP+levodopa [2 mg/kg] [Sigma Aldrich]), (4) MPTP+Hepad 1 (200 mg/kg), (5) MPTP+Hepad 1 (300 mg/kg), (6) MPTP+Hepad 1 (400 mg/kg), (7) MPTP+Hepad 2 (200 mg/kg), (8) MPTP+Hepad 2 (300 mg/kg), and (9) MPTP+Hepad 2 (400 mg/kg). The mice in the sham group had a normal diet for 28 days, and the mice in the MPTP treatment group (group 2) were intraperitoneally injected MPTP of 20 mg/kg/day for 28 days. In groups 3-9, MPTP was administered 20 mg/kg/day for 7 days, and then, levodopa (2 mg/kg/day), Hepad 1 (200, 300, and 400 mg/kg/day), and Hepad 2 (200, 300, and 400 mg/kg/day) were orally administered to the mice for 21 days. After 28 days, the mice were sacrificed by decapitation following a 16-h fast (FIG. 7). The brains were dissected and analyzed by histological and western blotting analysis. The brain tissues were stored at −70° C. in a deep freezer until use.

Histological Analysis

Brain specimens (4 μm) were fixed in 10% formaldehyde for 24 h and were embedded in paraffin. The sections were stained with H&E for routine histopathological examination and were assessed using a light microscope (Nikon, Eclipse TE 200, Tokyo, Japan) at 100× magnification.

Immunohistochemical Staining

Brain sections (4 μm thick) were deparaffinized in xylene-alcohol series for 5 min each, with subsequent recovery of antigenic sites on steam fluent (pot value) for 30 min. The slides were washed twice for 5 min with 1× phosphate-buffered saline (PBS) and then immersed in 0.3% hydrogen peroxide for 30 min at 25° C. to block endogenous peroxidase activity. The sections were incubated with 10% goat serum (for polyclonal antibodies) for 30 min and then incubated at 4° C. with the TH primary antibody (Abcam, Cambridge, UK) for 24 h. Subsequently, all samples were incubated with biotinylated goat anti-rabbit IgG (H+L) horseradish peroxidase (HRP)-conjugated antibodies (Zymax). The sections were incubated with 3,3-diaminobenzidine (Vectro Laboratories, Inc., Burlingame, Calif., USA) for 10 min at 37° C. Finally, the tissue sections were counterstained with hematoxylin for 2 min, dehydrated with an alcohol-xylene series, and mounted with coverslips using Permount mounting medium (Thermo Fisher Scientific). The specimens were examined using a Nikon Eclipse TS100 microscope (Nikon, Tokyo, Japan) at 200× magnification, and the microscopy images were analyzed using the OptiView image analysis software (Korea Lab Tech, Seongnam-si, Republic of Korea). Immunopositive neurons were counted manually.

Western Blotting Analysis

Mouse brains were lysed in radioimmunoprecipitation assay lysis buffer containing protease inhibitor (Roche, Mannheim, Germany) and centrifuged at 10,000×g for 30 min at 4° C. Total protein levels were determined using a Bio-Rad protein kit (Bio-Rad, Hercules, Calif., USA). The proteins were electrophoresed by a 10-15% sodium dodecyl sulfate-polyacrylamide gel and transferred onto the Immobilon-P transfer membrane (EMD Millipore Co., Bedford, Mass., USA). The membrane was blocked with 5% bovine serum albumin (Sigma-Aldrich). Subsequently, the membrane was incubated at 4° C. for 24 h with the following primary antibodies: (3-actin (Cell Signaling Technology, Beverly, Mass., USA), TNF-α (Abcam), IL-6 (Santa Cruz Biotechnology), Mac-1 (Bio-Rad, CA, USA), iNos (Abcam), COX-2 (Abcam), Bcl-2 (Abcam), GST (Cell Signaling Technology), SOD-1 (Santa Cruz Biotechnology, Santa Cruz, Calif., USA), NOX-4 (Novusbio, CO, USA), Bax (Cell Signaling Technology), caspase-3 (Abcam), cytochrome C (Abcam), PARP-1 (Abcam), p-AKT (Cell Signaling Technology), p-ERK (Cell Signaling Technology), and p-JNK (Cell Signaling Technology). The membranes were subsequently incubated with goat anti-rabbit IgG (H+L) HRP-conjugated secondary antibody (Zymax, San Francisco, Calif., USA). Protein bands were detected using a chemiluminescence method (Thermo Fisher Scientific, Waltham, Mass., USA) by a C-DiGit Blot Scanner (Li-COR, NE, USA), and their densities were quantified using ImageJ (NIH, Rockville, Md., USA). All data were normalized to the (3-actin values.

Statistical Analysis

All statistical analyses were performed using SPSS version 18.0 (IBM, Chicago, Ill., USA). One-way analysis of variance with Duncan's post-hoc test was used to determine the significance of differences in mean values ($p<0.05$) between experimental groups. Data of each test are presented as mean±standard deviations.

Figure 9:
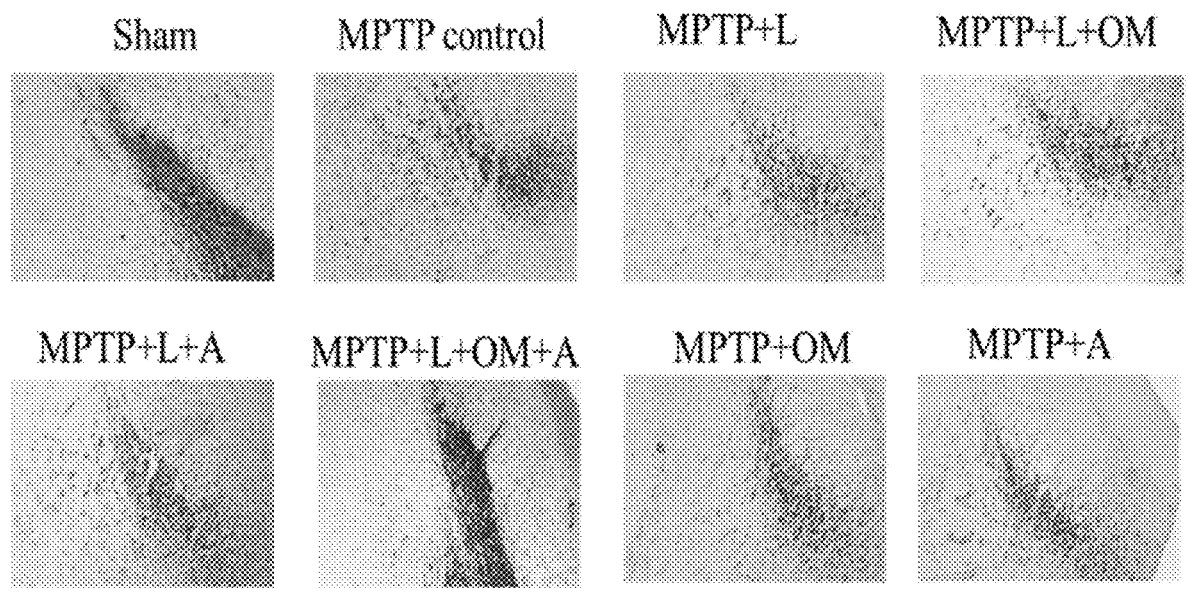
FIG. 9 shows immunohistochemical staining of tyrosine hydroxylase (TH)-positive neurons.

Example 12. Immunohistochemical Detection of Tyrosine Hydroxylase (TH) and Hematoxylin and Eosin (H&E) Staining and in the Substantia Nigra of Rats The histological examination showed that tyrosine hydroxylase (TH) expression reduced prominently after MPTP injection (FIG. 9). The up-regulation of TH expression in substantia nigra and ventral tegmental area were shown in all the Hepad s7 (Hs7) strategized groups, either with or without levodopa treatment.

Figure 10:
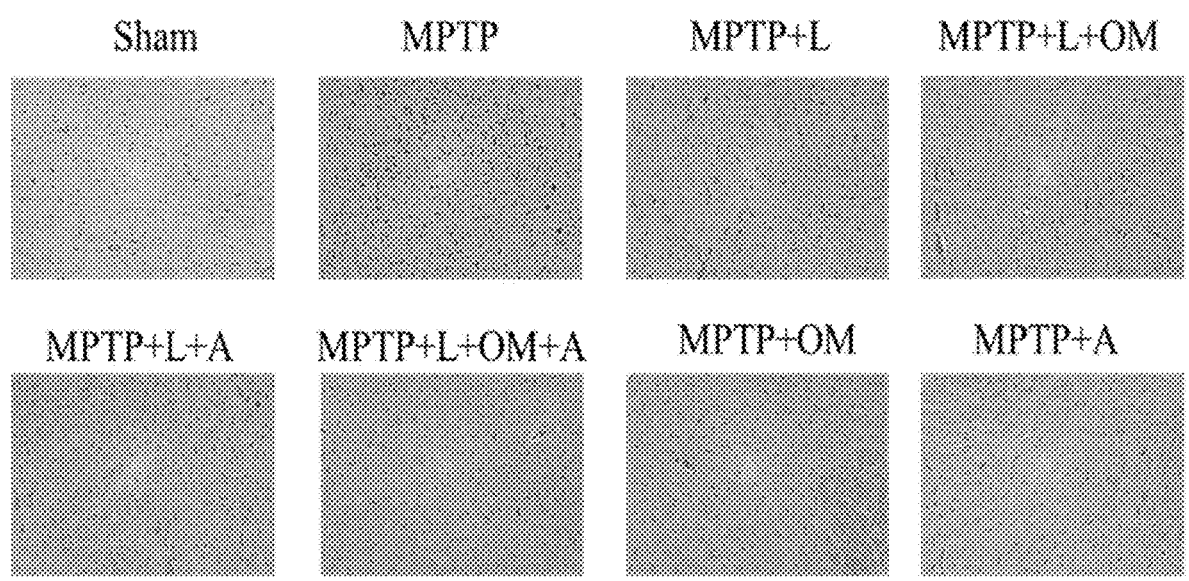
FIG. 10 shows exemplary photomicrographs (100× magnification) of hematoxylin and eosin-stained brain sections.

Lewy bodies were observed as spherical bodies, each with a dense core surrounded by a halo, in MPTP-intoxicated mice compared with the sham mice (FIG. 10). MPTP-intoxicated mice showed dopaminergic neuronal damage with loss of multipolar shape and distorted nuclei (FIG. 10). Notably, multipolar neurons with nucleoli and basophilic granular cytoplasm were observed in the SNpc in Hs7-treated rats.

The results further demonstrated that Hs7 exhibited better mitigation effects than the positive control, levodopa. Also, the combined treatment groups with levodopa and Hs7 (300 mg/kg, OM(P.O.))+Hs7 (acupunctural injection 1.7 ml/kg, I.V. (intravenous injection)) group allows a higher number of viable DA neurons to survive, which showed a pronounced neuroprotective effect on DA neurons recovery.

Example 13. Synergist Effects of Hs7 of Levodopa on MPTP-Induced Inflammatory Responses To investigate the synergistic effects of levodopa to inhibit the inflammatory response induced by the MPTP treatment, whether levodopa (L) combined with oral administration (OM) and acupunctural injection (A) of Hs7 would affect the activation of macrophage-1 (Mac-1), inducible nitric oxide synthase (iNOS), COX-2, phosphorylated I$\kappa$B-$\alpha$ (p-I$\kappa$B-$\alpha$), IL-6, and TNF-$\alpha$ was examined. Inflammatory responses were activated in rats with the MPTP administration.

Figure 11:
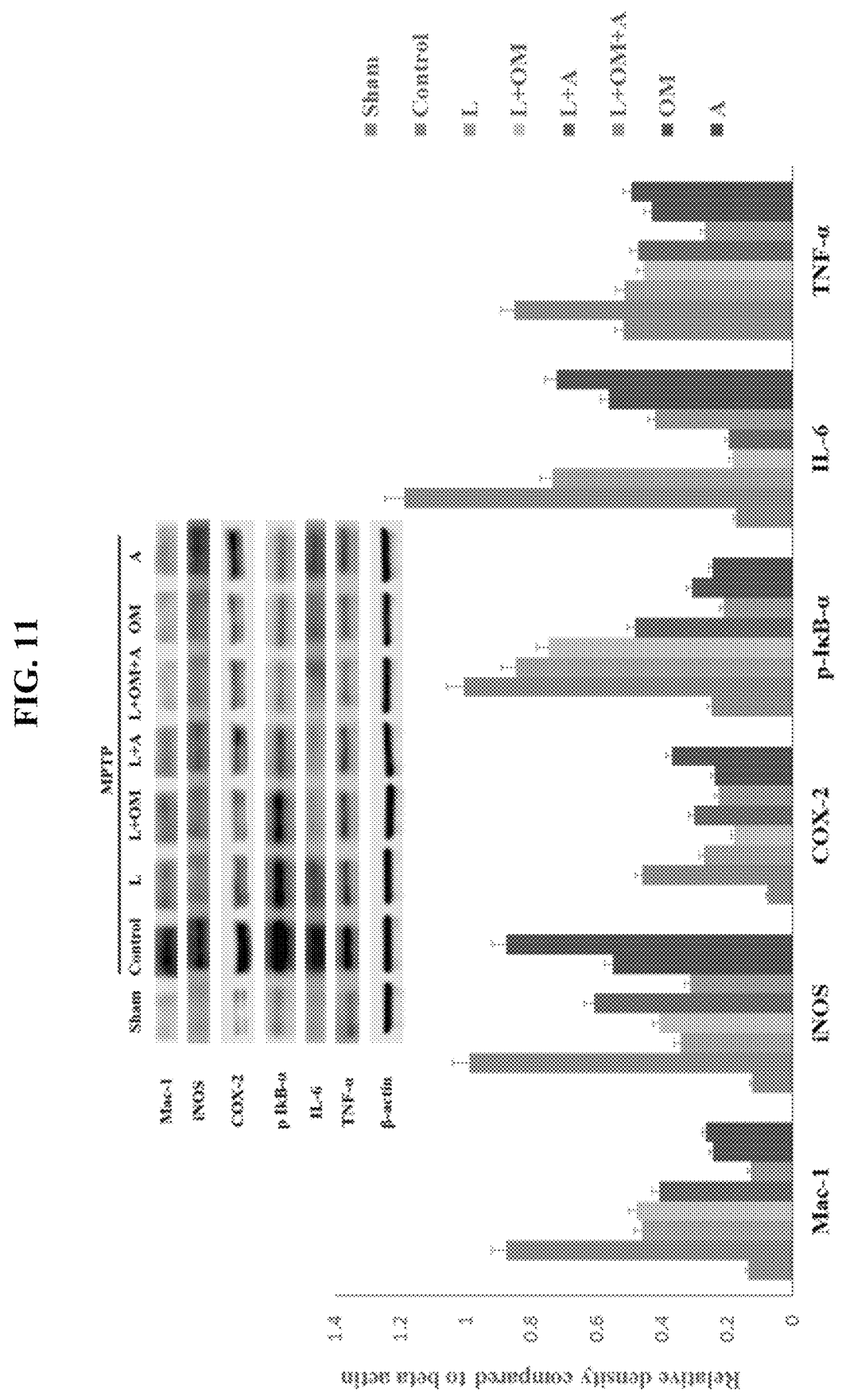

As shown in FIG. 11, the expression of Mac-1 protein was significantly elevated (by 6.4-fold) in MPTP control groups when compared with the protein expression in sham groups. However, by comparison to the control groups, the elevated level of MAC-1 proteins were considerably attenuated in L (by 1.9 fold), L+OM (by 1.8 fold), L+A (by 2.2 fold), L+OM+A (6.7 fold), OM (3.6 fold), and A groups (by 3.3 fold). The expression of Mac-1 protein was markedly reduced (by 0.9-fold) in L+OM+A groups, compared with sham groups.

In addition, the iNOS protein expression level in MPTP control group was 8.0 fold higher than the iNOS level in the sham group. By contrast, this elevated expression of iNOS level in the MPTP control group was significantly inhibited in L (by 2.9-fold), L+OM (by 2.3-fold), L+A (by 1.6-fold), L+OM+A (by 3.1-fold), OM (1.8-fold), and A groups (by 1.1-fold).

Moreover, with reference to the COX-2 level in the sham operated group, the MPTP-intoxicated group overexpressed the COX-2 protein by 6-fold. But, in animals treated with drugs, the expression level of COX-2 was notably down-regulated by 1.7-fold (L group), 2.6-fold (L+OM group), 1.5-fold (L+A group), 2.0-fold (L+OM+A group), 1.9-fold (OM group), and 1.3-fold (A group), respectively.

Furthermore, it is noted that the expression of p-I$\kappa$B-$\alpha$ protein was dramatically elevated after MPTP intoxication (4.1 fold higher than sham group) and that the synergistic effects of levodopa slightly restored the p-I$\kappa$B-$\alpha$ level to its baseline value. Therefore, compared to MPTP control group, the p-I$\kappa$B-$\alpha$ level were significantly reduced in L (by 1.2-fold), L+OM (by 1.4-fold), L+A (by 2.1-fold), L+OM+A (by 4.8-fold), OM (by 3.3-fold) and A groups (by 4.1-fold).

Additionally, the expression level of IL-6 protein was significantly elevated in MPTP-intoxicated (6.8-fold) compared with sham operated rats. However, when compared to the MPTP groups, this increase in IL-6 level was notably attenuated in L (by 1.6-fold), L+OM (by 6.4-fold), L+A (by 6.0-fold), L+OM+A (by 2.8-fold), OM (by 2.1-fold) and A groups (by 1.6-fold).

Also, a significant elevation in the TNF-$\alpha$ protein expression level was found in MPTP-intoxicated rats (1.7-fold) compared with the expression level in sham groups. By contrast, the TNF-$\alpha$ protein activation induced by MPTP administration were markedly declined in L (by 1.7-fold), L+OM (by 1.9-fold), L+A (by 1.8-fold), L+OM+A (by 3.2-fold), OM (by 2.0-fold) and A groups (by 1.7-fold).

These results indicate that oral administration (OM) and acupunctural injection (A) of Hs7 exhibit an efficient synergistic effect with levodopa to inhibit the inflammation-related proteins, such as MAC-1, iNOS, COX-2, p-I$\kappa$B-$\alpha$, IL-6, and TNF-$\alpha$, supporting that Hs7 (Hepad s7) mitigates PD-associated pathology.

Example 14. Materials and Methods Used in Examples 12-13

Preparation of Sample

Hs7 contains *Uncariae Ramulus, Paeonia japonica, Machilus thunbergii*, Black pepper, *panax ginseng* C. A Meyer, *Glycyrrhiza uralensis, Mucunae caulis*, and optionally additional herbs. The herbs were extracted in boiling water for 24 h, and the extracts were then collected and filtered. Subsequently, the filtrate was concentrated under reduced pressure at 50° C.

Animal Experiments

Figure 8:
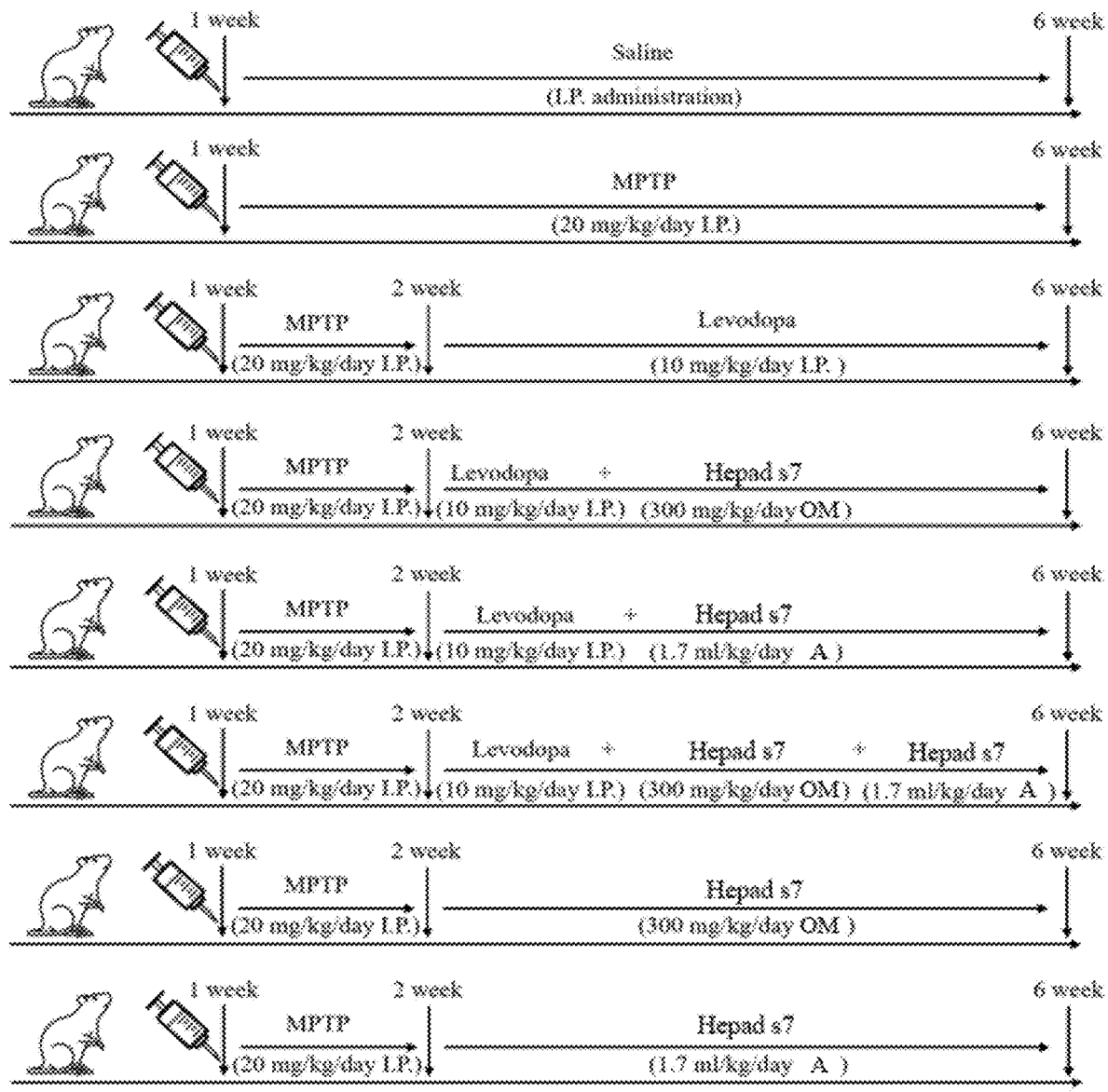
FIG. 8 shows an exemplary flowchart depicting the timeline of the experimental procedures, as described in Examples 12-13. "OM" indicates oral administration of Hs7; and "A" indicates acupunctural injection (I.V. injection) of Hs7.

Four-week-old male SD rats were purchased from Rion Bio, Inc. and were housed in a temperature-controlled (21-22° C.) and light-controlled (12 h light/dark cycle) environment with 70% humidity; they were given free access to water and rodent chow. After a 1-week period of adaptation, the rats were randomly divided into eight groups (n=8) for MPTP and Hepad s7 studies: (l) normal (sham) group, (2) MPTP-intoxicated group, (3) positive group (MPTP+levodopa [10 mg/kg] [Sigma Aldrich]), (4) MPTP+levodopa [10 mg/kg]+Hepad s7 (300 mg/kg, P.O. (OM: oral administration)), (5) MPTP+levodopa [10 mg/kg]+Hepad s7 (acupunctural injection 1.7 ml/kg, I.V. (A)), (6) MPTP+levodopa [10 mg/kg]+Hepad s7 (300 mg/kg, P.O. (OM))+Hepad s7 (acupunctural injection 1.7 ml/kg, I.V. (A)), (7) MPTP+Hepad s7 (300 mg/kg, P.O. (OM)), (8) MPTP+Hepad s7 (acupunctural injection 1.7 ml/kg, I.V. (A)). The rats in the sham group (group 1) had a normal diet for 35 days, and the rats in the MPTP-intoxicated group (group 2)

were intraperitoneally injected with MPTP (20 mg/kg/day) for 35 days. In groups 3-8, MPTP (20 mg/kg/day) was administered for 7 days; then, levodopa (10 mg/kg/day) was treated for 28 days, Hepad s7 (300 mg/kg/day) were orally administered (P.O. (OM)) to the rats for 28 days, and/or Hepad s7 (acupunctural injection 1.7 ml/kg/day (A)) were intravenously treated (I.V.) by acupunctural injection for 28 days according to the group designations listed above. After 35 days, the rats were sacrificed by decapitation following a 16-h fast (FIG. 8). The brains were dissected and analyzed by histological and western blotting analysis. The brain tissues were stored at −70° C. in a deep freezer (ILSIN-TECH, Daejeon, Korea) until analysis.

Histological Analysis

Brain specimens (4 μm) were fixed in 10% formaldehyde for 24 h and were embedded in paraffin. The sections were stained with H&E for routine histopathological examination and were assessed using a light microscope (Nikon, Eclipse TE 200, Tokyo, Japan) at 100× magnification.

Immunohistochemical Staining

Brain sections (4-μm thick) were deparaffinized in a xylene-alcohol series for 5 min each, with subsequent recovery of antigenic sites on steam fluent (pot value) for 30 min. The slides were washed twice for 5 min each with 1× phosphate-buffered saline (PBS), then immersed in 0.3% hydrogen peroxide for 30 min at 25° C. to block endogenous peroxidase activity. The sections were incubated with 10% goat serum (for polyclonal antibodies) for 30 min and then incubated at 4° C. with primary antibody against TH (Abcam, Cambridge, UK) for 24 h. Subsequently, all samples were incubated with biotinylated goat anti-rabbit IgG (H+L) horseradish peroxidase (HRP)-conjugated antibodies (Zymax, San Francisco, Calif., USA). The sections were incubated with 3,3-diaminobenzidine (Vector Laboratories, Inc., Burlingame, Calif., USA) for 10 min at 37° C. Finally, the tissue sections were counterstained with hematoxylin for 2 min, dehydrated with an alcohol-xylene series, and mounted with coverslips using Permount mounting medium (Thermo Fisher Scientific, Waltham, Mass., USA). The specimens were examined using a Nikon Eclipse TS100 microscope (Nikon, Tokyo, Japan) at 200× magnification, and the microscopy images were analyzed using the OptiView image analysis software (Korea Lab Tech, Seongnam-si, Republic of Korea). Immunopositive neurons were counted manually.

Western Blotting Analysis

Rat brains were lysed in radioimmunoprecipitation assay lysis buffer containing protease inhibitor (Roche, Mannheim, Germany) and centrifuged at 10,000×g for 30 min at 4° C. Total protein levels were determined using a Bio-Rad protein kit (Bio-Rad, Hercules, Calif., USA). The proteins were separated by electrophoresis in a 10-15% sodium dodecyl sulfate-polyacrylamide gel and transferred onto the Immobilon-P transfer membrane (EMD Millipore Co., Bedford, Mass., USA). The membrane was blocked with 5% bovine serum albumin (Sigma-Aldrich). Subsequently, the membrane was incubated at 4° C. for 24 h with primary antibodies against one of the following proteins: (3-actin (Cell Signaling Technology, Beverly, Mass., USA), TNF-α (Abcam), IL-6 (Santa Cruz Biotechnology, Santa Cruz, Calif., USA), Mac-1 (Bio-Rad, CA, USA), iNos (Abcam), COX-2 (Abcam), Bcl-2 (Abcam), GST (Cell Signaling Technology), SOD-1 (Santa Cruz Biotechnology), NOX-4 (Novusbio, Littleton, Colo., USA), Bax (Cell Signaling Technology), caspase-3 (Abcam), cytochrome C (Abcam), PARP-1 (Abcam), p-AKT (Cell Signaling Technology), p-ERK (Cell Signaling Technology), and p-JNK (Cell Signaling Technology). The membranes were subsequently incubated with goat anti-rabbit IgG (H+L) HRP-conjugated secondary antibody (Zymax). Protein bands were detected using a chemiluminescence method (Thermo Fisher Scientific) by a C-DiGit Blot Scanner (Li-COR, Lincoln, Nebr., USA), and their densities were quantified using ImageJ (NIH, Rockville, Md., USA). All data were normalized to the (3-actin values.

Statistical Analysis

All statistical analyses were performed using SPSS version 18.0 (IBM, Chicago, Ill., USA). One-way analysis of variance with Duncan's post hoc test was used to determine the significance of differences in mean values (p<0.05) between experimental groups. Data for each test are presented as mean±standard deviations.

Figure 12A:
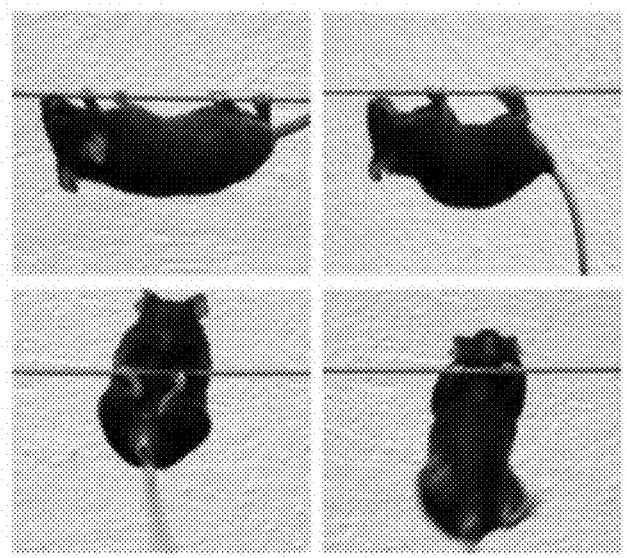
FIG. 12A shows exemplary mouse responses during the wire hanging test.
Figure 12B:
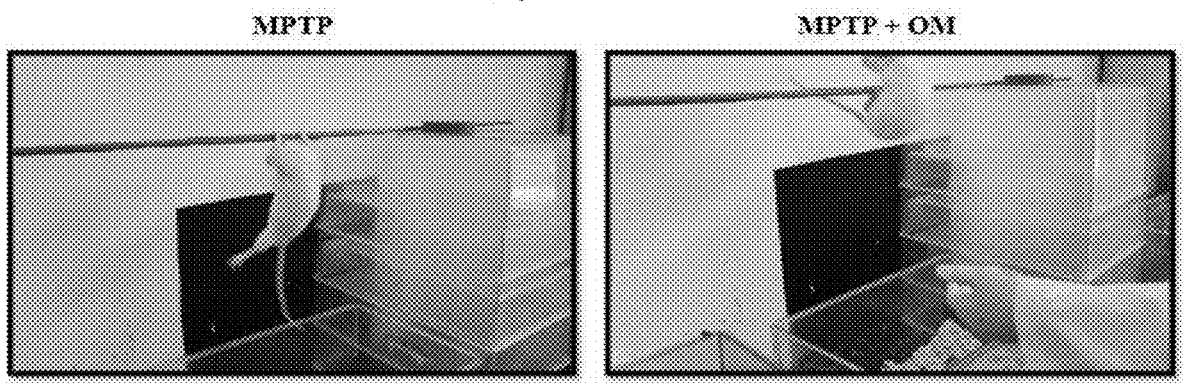
FIG. 12B shows exemplary responses of the mouse treated only with MPTP and the mouse treated with MPTP and co-treated with Hs7.

Example 15. Acupunctural Injection of Hs7, Oral Administration of Hs7, and Acupunctural Injection Combined with Oral Administration of Hs7 Result in More Neuromuscular Strength than Levodopa Treatment in the MPTP-Induced PD Mouse Model Wire hanging test is a method to assess muscle function and coordination over time. The test is based on the latency of a mouse to fall off a metal wire upon exhaustion. The wire hanging test is designed to demonstrate a motor neuromuscular impairment and motor coordination. This test is also used for evaluating the neuromuscular tone. A 55 cm wide 2 mm thick wire is secured to two vertical stands. The wire must be tightly attached to the frame to avoid vibration or unwanted displacement of the wire, while the investigator is handling the animals or during the measurements, since these unwanted effects would interfere with the animal's performance (FIG. 12A).

Wire hanging test was performed to assess the neuromuscular ability of mice. By performing this test, the measure of motor coordination and animal's ability to take on its hind limbs and tail with a specific end goal to grasp wire was observed. Latency to fall was measured from the time a mouse hanged by its forepaws till it falls.

Figure 12C:
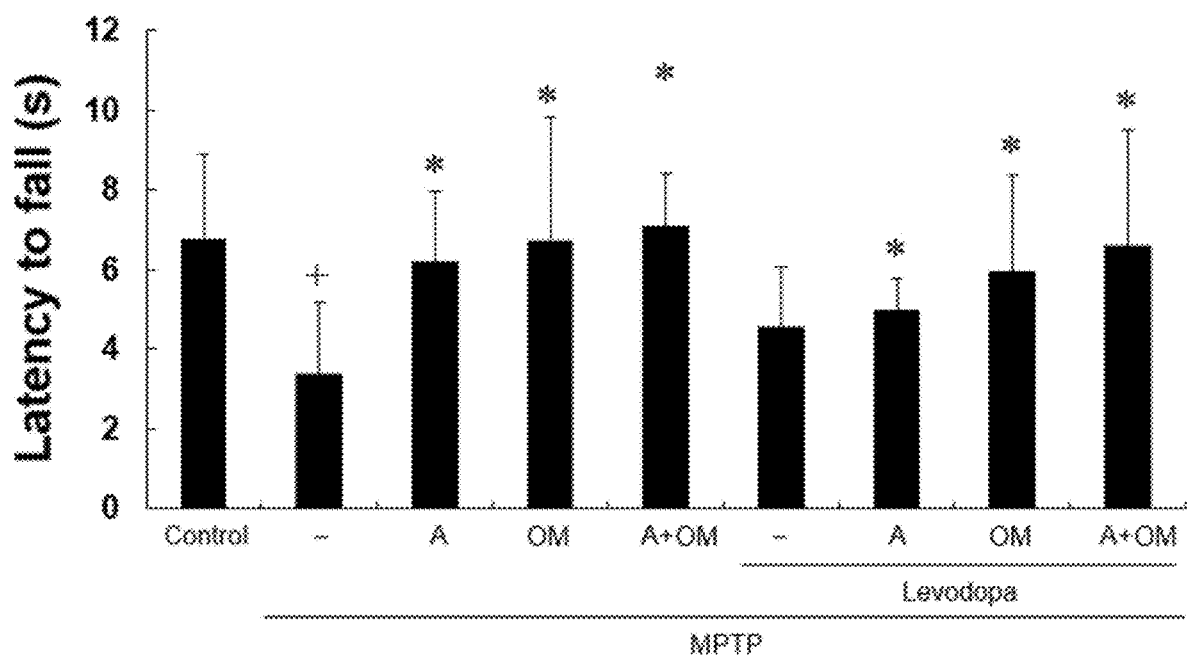
FIG. 12C shows effects of Hs7 via acupunctural injection (A) and oral administration (OM) on the neuromuscular ability of the PD mouse model. "A" indicates acupunctural injection of Hs7 and "OM" indicates oral administration of Hs7. "+" indicates $p<0.005$ (versus control untreated with MPTP), and "*" indicates $p<0.05$ (versus treated only with MPTP).

As shown in FIG. 12C, acupunctural injection of Hs7, oral administration of Hs7, and acupunctural injection combined with oral administration of Hs7 result in more neuromuscular strength than levodopa treatment in the MPTP-induced PD mouse model.

Unless defined otherwise, all technical and scientific terms and any acronyms used herein have the same meanings as commonly understood by one of ordinary skill in the art in the field of this invention.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein can be employed in practicing the present disclosure. It is intended that the following claims define the scope of the present disclosure and that methods and structures within the scope of these claims and their equivalents be covered thereby.

What is claimed is:

1. A method of treating a disorder characterized by neuro-inflammation, neuro-apoptosis, or neuro-oxidative damage in a subject in need thereof, comprising administering to the subject a pharmaceutical composition that comprises an herbal extract of *Paeonia japonica, Uncariae ramulus, Machilus thunbergii, Panax ginseng* C. A Meyer, *Glycyrrhiza uralensis, Mucunae caulis*, and black pepper, wherein the herbal extract is present in the pharmaceutical composition in an effective amount to reduce or delay a sign or a symptom of the disorder, and a pharmaceutically acceptable carrier,
   wherein the administering is effective to treat the disorder in the subject, and
   wherein the disorder is Parkinson's disease.

2. The method of claim 1, wherein the pharmaceutical composition is administered by oral administration, acupunctural injection, intravenous injection, or a combination thereof.

3. The method of claim 1, wherein the pharmaceutical composition is administered in one or more doses.

4. The method of claim 3, wherein the one or more doses of the pharmaceutical composition are delivered via a same route or via different routes.

5. The method of claim 1, wherein the method further comprises administering a secondary therapeutic regimen, agent, or treatment in conjunction with the pharmaceutical composition simultaneously, previously, or subsequently.

6. The method of claim 5, wherein the secondary therapeutic regimen, agent, or treatment is levodopa.

7. The method of claim 1, wherein the sign or the symptom is a neuronal cell death, an inflammation, an oxidative stress, a motor deficit, or a combination thereof.

\* \* \* \* \*